(12) United States Patent
Tu

(10) Patent No.: US 11,571,562 B2
(45) Date of Patent: Feb. 7, 2023

(54) SHAPE CUTTING DEVICE FOR SKIN ELECTRODE PATCH

(71) Applicant: Feng Ching Tu, New Taipei (TW)

(72) Inventor: Feng Ching Tu, New Taipei (TW)

( * ) Notice: Subject to any disclaimer, the term of this patent is extended or adjusted under 35 U.S.C. 154(b) by 294 days.

(21) Appl. No.: 17/072,559

(22) Filed: Oct. 16, 2020

(65) Prior Publication Data

US 2021/0031027 A1 Feb. 4, 2021

Related U.S. Application Data

(63) Continuation-in-part of application No. 15/357,088, filed on Nov. 21, 2016, now Pat. No. 10,843,365.

(51) Int. Cl.
*A61N 1/04* (2006.01)
*B26F 1/44* (2006.01)
*B26D 7/26* (2006.01)

(52) U.S. Cl.
CPC ......... *A61N 1/0492* (2013.01); *B26D 7/2614* (2013.01); *B26F 1/44* (2013.01); *B26F 2001/4472* (2013.01)

(58) Field of Classification Search
CPC .... B26F 1/384; B26F 1/44; B26F 2001/4472; B26D 7/0625; B26D 7/2614; A61N 1/0492
See application file for complete search history.

(56) References Cited

U.S. PATENT DOCUMENTS

| | | | |
|---|---|---|---|
| 1,701,240 A * | 2/1929 | MacLean | B31D 1/025 493/480 |
| 3,383,969 A | 5/1968 | Saunders et al. | |
| 4,085,639 A | 4/1978 | Marconi | |
| 4,248,117 A | 2/1981 | Bugnone | |
| 4,613,321 A * | 9/1986 | Kesten | B26D 11/00 493/373 |
| 4,635,642 A | 1/1987 | Cartmell et al. | |
| 4,795,516 A | 1/1989 | Strand | |
| 4,798,642 A | 1/1989 | Craighead et al. | |
| 5,405,486 A | 4/1995 | Sablotsky et al. | |
| 5,713,128 A | 2/1998 | Schrenk et al. | |

(Continued)

FOREIGN PATENT DOCUMENTS

| | | | | |
|---|---|---|---|---|
| CN | 108705605 A | * | 10/2018 | |
| EP | 0321590 A2 | * | 12/1987 | B23P 15/40 |
| WO | WO-2010018703 A1 | * | 2/2010 | B26D 5/005 |

*Primary Examiner* — Jeffrey T Carley

(74) *Attorney, Agent, or Firm* — Muncy, Geissler, Olds & Lowe, P.C.

(57) ABSTRACT

A shape cutting device of a skin electrode patch includes: a substrate conveyor for transmitting a coated substrate portion and a conductive adhesive portion; a positioning conveyor; a fitted shape cutting module installed in a successive portion of the positioning conveyor and having two pressing wheels and a shape cutting unit, and the two pressing wheels being provided for pressing the coated substrate portion and the conductive adhesive portion, and the shape cutting unit including a roller body with at least one cutting knife which is in a geometrical shape and includes two side cutters and a first-end cutter at an axial end, and opposite ends of the first-end cutter having two second-end cutters, and a gap being formed in the two second-end cutters. The cutting knife has a design that integrates the transmission feature and the efficiency of the whole production line.

9 Claims, 24 Drawing Sheets

(56) References Cited

U.S. PATENT DOCUMENTS

| | | | | |
|---|---|---|---|---|
| 5,829,121 | A | * | 11/1998 | Shoemaker ........ H01Q 21/0087 |
| | | | | 29/601 |
| 5,967,009 | A | | 10/1999 | Truttmann et al. |
| 2002/0056513 | A1 | * | 5/2002 | Tabuchi ................ B65C 9/1819 |
| | | | | 156/267 |
| 2003/0134545 | A1 | | 7/2003 | McAdams et al. |
| 2004/0261939 | A1 | | 12/2004 | Ogle et al. |
| 2007/0039443 | A1 | | 2/2007 | Takahashi et al. |
| 2011/0056621 | A1 | | 3/2011 | Quinn |
| 2012/0077661 | A1 | | 3/2012 | Oonishi et al. |
| 2013/0023816 | A1 | * | 1/2013 | Bachinski .......... A61N 1/36014 |
| | | | | 604/20 |
| 2013/0145916 | A1 | * | 6/2013 | Nordlin .................. B26F 1/386 |
| | | | | 29/428 |
| 2015/0044338 | A1 | | 2/2015 | Nagle et al. |
| 2015/0313499 | A1 | | 11/2015 | Sohn |
| 2017/0239832 | A1 | * | 8/2017 | Tsuji ...................... B26D 7/265 |

\* cited by examiner

SHAPE CUTTING DEVICE FOR SKIN ELECTRODE PATCH

CROSS REFERENCE TO RELATED APPLICATIONS

This application is a Continuation-in-Part of co-pending application Ser. No. 15/357,088, filed on 21 Nov. 2016, for which priority is claimed under 35 U.S.C. § 120, the entire contents of all of which are hereby incorporated by reference.

FIELD OF THE INVENTION

The present invention relates to a shape cutting device of a skin electrode patch, and more particularly to the device used for shape cutting or material cutting in the manufacture of skin electrode patches, and the device provides a continuous cutting effect and a strong structural strength to prevent breakdowns in production lines.

BACKGROUND OF THE INVENTION

1. Description of the Related Art

Present electrode skin treatment devices used for treating or soothing various types of nervous and muscular pains and have the effects of improving neuromuscular excitability, adjusting meridian functions and enhancing blood circulation. The electrode treatment devices are usually used together with a skin electrode patch, and the skin electrode patch is attached to a position of a human body to be treated or soothed, the skin electrode patch conceals a power supply device and circuits capable of generating a pulse output of positive and negative electrodes therein, so that the external appearance shows a structure of a seamless waterproof object, and the skin electrode patch is a self-adhesive patch capable of generating electrode pulses.

With reference to FIGS. 1 and 1a for the assembly and manufacture of a conventional electrode patch, a shape cutting device 90 is provided for cutting a patch material strip 92 into a specific shape, and the shape cutting device 90 has a cutting knife 91, and the cutting knife 91 cuts the patch material strip 92 equidistantly into plural pieces of electrode patches 93, wherein the electrode patch 93 needs to manufacture an electrode lead 94 separately, and an end of the electrode lead 94 is a power connector 941, and the power connector 941 acts as an input channel of an external power supply, and the other end of the electrode lead 94 opposite to the power connector 941 is an exposed conductive terminal 942, and the power connector 941 and the exposed conductive terminal are electrically conducted with one another.

Wherein, the electrode patch 93 includes a coated substrate layer 931 and a conductive adhesive layer 932, and a glue layer 9311 is adhered to a side of the coated substrate layer 931. The conductive adhesive layer 932 includes an adhesive layer body 9321, and a conductive layer 9322 is adhered to a side of the adhesive layer body 9321, and a release layer 9323 (such as a release paper) is attached onto the other side of the adhesive layer body 9321. During assembling, the glue layer 9311 of the coated substrate layer 931 is adhered with the exposed conductive terminal 942 of the electrode lead 94, and then the coated substrate layer 9311 and the conductive adhesive layer 932 are laminated and adhered with one another, so that the electrode lead 94 is fixed between the coated substrate layer 931 and the conductive adhesive layer 932, and the electrode lead 94 and the conductive layer 9322 are electrically conducted with one another. Now, the power connector 941 of the electrode lead 94 is protruded to the outside as shown in the figure.

In the assembling and manufacturing method of the aforementioned skin electrode patch 93, each step is performed manually, and the skin electrode patch 93 must be cut into a specific shape first, and then the electrode lead 94 is installed to the coated substrate layer 931 or the conductive adhesive layer 932 manually before the lamination process takes place. Obviously, the conventional method is unfavorable to enhancing the assembling speed of the production line and requires further improvements. Therefore, it is an important subject for related manufacturers and designer to develop and design a novel electrode patch to overcome the drawbacks of the conventional electrode patch.

In view of the drawbacks of the conventional electrode patch and its manufacturing method, the inventor of the present invention based on years of experience in the related industry to conduct researches and experiments and finally developed a shape cutting device of a skin electrode patch in accordance with the present invention with manufacturing convenience and efficiency.

2. Summary of the Invention

Therefore, it is a primary objective of the present invention to provide a shape cutting device of a skin electrode patch that allows the electrode lead to be assembled and installed conveniently in a production line during the electrode patch manufacturing process.

Another objective of the present invention is to provide a roller type configuration of the cutting knife to facilitate improving the shape cutting efficiency.

To achieve the aforementioned and other objectives, the present invention discloses a shape cutting device of a skin electrode patch, comprising: a substrate conveyor, for transmitting a strip coated substrate portion and a conductive adhesive portion; a positioning conveyor, including a conveyor belt; a fitted shape cutting module, installed in a successive portion of the positioning conveyor, and having two pressing wheels and a shape cutting unit, and the two pressing wheels pressing the coated substrate portion and the conductive adhesive portion, and the shape cutting unit including a roller body, and the roller body having at least one cutting knife installed thereon, and the cutting knife being in a geometrical shape and including the cutting knife having two protruding side cutters and a first-end cutter of an axial end, and opposite ends of the first-end cutter having two second-end cutters, and the first-end cutter being coupled to the side cutters on both sides, and the two side cutters and the two second-end cutters being coupled to one another, and a shape cutting area inside the cutting knife being formed and enclosed by the first-end cutter, the two side cutters and the two second-end cutters, and a gap being formed between the two second-end cutters; wherein, the cutting knife is used for cutting the coated substrate portion, an attached body of the conductive adhesive portion into a shape.

In the shape cutting device, the conveyor belt has a plurality of positioning tools for positioning an electrode lead.

In the shape cutting device, the roller body is installed to a driving shaft.

In the shape cutting device, the cutting knife includes two protruding side cutters and a first-end cutter at an axial end, and opposite ends of the first-end cutter have two second-end cutters, and the first-end cutter and the side cutter on both sides are coupled to one another, and the two side cutters and the two second-end cutters are coupled to one another, such that a shape cutting area inside the cutting knife is formed and enclosed by the first-end cutter, the two side cutters and the two second-end cutters, and a gap is formed between the two second-end cutters.

The present invention further provides a shape cutting unit of a skin electrode patch, and the shape cutting unit further comprises a driving shaft and a roller body, and the roller body has at least one cutting knife and the cutting knife is substantially in a geometrical shape, and the cutting knife includes two protruding side cutters and first-end cutter of an axial end, and opposite ends of the first-end cutter have two second-end cutters respectively, and the first-end cutter is coupled to the side cutters on both sides, and the two side cutters are coupled to the two second-end cutters, and a shape cutting area inside the cutting knife is formed and enclosed by the first-end cutter, the two side cutters and the two second-end cutters, and a gap is formed between the two second-end cutters.

In the shape cutting unit, the cutting knife is substantially in an arc shape, and the first-end cutter, the side cutter, and the second-end cutter of the cutting knife form an end and two side edges of the arc shaped cutting knife, and the gap forms the other end gap of the arc shaped cutting knife.

A further objective of the present invention is to provide a cutting knife capable of completing the manufacture of the electrode patch after the cutting process by the cutting knife without requiring any subsequent assembling or operating processes of the electrode lead and the cutting knife features high convenience and efficiency of cutting the electrode patches in the assembling process.

To achieve the aforementioned and other objectives, the present invention provides a shape cutting device for skin electrode patch, and the shape cutting device comprises a stamping shaft and a cutting tool holder coupled to each other, wherein the cutting tool holder has a cutting tool surface; at least one cutting knife is disposed on the cutting tool surface; the cutting knife is in a geometric shape; the cutting knife comprises two protruding side cutters and a first-end cutter; the first-end cutter is disposed adjacent to an end of the cutting tool holder; the first-end cutter has at least two opposite ends, and each opposite end of the first-end cutter has a second-end cutter; the first-end cutter is coupled to the side cutters on both sides; the two side cutters are coupled to the two second-end cutters respectively; a cutting area inside the cutting knife is formed and enclosed by the first-end cutter, the two side cutters and the two second-end cutters; only one gap is formed between the two second-end cutters of the cutting knife and disposed at a non-contact position of the two second-end cutters; the cutting knife is continuous and complete from a second-end cutter of the two second-end cutters to the other second-end cutter of the two second-end cutters; and the gap is provided for preventing an electrode lead from being cut off.

In the shape cutting device, the cutting tool surface is a horizontal cutting tool surface.

In the shape cutting device, the cutting knife is in a square shape or a rectangular shape.

In the shape cutting device, the cutting knife is in a circular shape, an elliptical shape, or an egg shape.

In the shape cutting device, the stamping shaft and the cutting tool holder are integrally combined into a stamping shaft body and the stamping shaft body is provided for installing the cutting knife.

In the shape cutting device, the first-end cutter is coupled to the two side cutters through a connection with a fillet or an arc-end angle, and the two side cutters are coupled to the two second-end cutters respectively through a connection with a fillet or an arc-end angle.

In the shape cutting device, the cutting knife cuts an electrode strip, and the electrode strip comprises a coated substrate portion and conductive adhesive portion with equivalent widths and bonded with each other, and a release layer linked with the bottom of the electrode strip, and the release layer is wider than and slightly protruded from the electrode strip.

In the shape cutting device, an electrode lead is clamped and positioned between the conductive adhesive portions and the coated substrate portion, and the electrode lead is protruded out from the electrode strip.

In the shape cutting device, the electrode strip has a strip edge, and the two second-end cutters are aligned precisely with or slightly protruded from the strip edge, and the strip edge is disposed on a side of the electrode strip where the electrode leads are protruding.

The present invention further provides a shape cutting device comprising a driving shaft and a cutting tool holder coupled to each other, and the cutting tool holder has a cutting tool surface, and the cutting tool surface has at least one cutting knife installed thereon, and the cutting knife is in a geometric shape, and the cutting knife comprises two protruding side cutters and a first-end cutter, and the first-end cutter is disposed adjacent to an end of the cutting tool holder, and the first-end cutter has at least two opposite ends, and an outer side of each opposite end of the first-end cutter has an end corner cutter with a fillet or an arc-end angle, and the first-end cutter and the side cutters on both sides are coupled to each other, and the two side cutters and the two end corner cutters are coupled to each other, and a cutting area inside the cutting knife is formed and enclosed by the first-end cutter, the two side cutters and the two second end corner cutters, and only one gap is formed between the two end corner cutters of the cutting knife, and the gap is disposed at a non-contact position of the two end corner cutters, and the cutting knife is continuous and complete from an end corner cutter of the two end corner cutters to the other end corner cutter of the two end corner cutters, and the gap is provided for preventing an electrode lead from being cut off.

In the shape cutting device, the driving shaft is a stamping shaft.

In the shape cutting device, the cutting tool surface is a horizontal cutting tool surface.

In the shape cutting device, the cutting knife is in a semicircular shape, a semi-elliptical shape, or a half-egg shape.

In the shape cutting device, the stamping shaft and the cutting tool holder are integrally combined into a stamping shaft body, and the stamping shaft body is provided for installing the cutting knife.

In the shape cutting device, the first-end cutter is coupled to the two side cutters through a connection with a fillet or an arc-end angle.

In the shape cutting device, the cutting tool holder is provided for installing a roller body of the cutting knife.

In the shape cutting device, the cutting knife cuts an electrode strip, and the electrode strip comprises a coated substrate portion and conductive adhesive portion with equivalent widths and bonded with each other, and a release layer linked with the bottom of the electrode strip, and the release layer is wider than and slightly protruded from the electrode strip.

In the shape cutting device, an electrode lead is clamped and positioned between the coated substrate portion and the conductive adhesive portion, and the electrode lead is protruded out from the electrode strip.

In the shape cutting device, the electrode strip has a strip edge, and the bottom edges of the two end corner cutters are aligned precisely with or slightly protruded out from the strip edge, and the strip edge is disposed on a side of the electrode strip where the electrode leads are protruding.

DESCRIPTION OF THE PREFERRED EMBODIMENTS

The above and other objects, features and advantages of this disclosure will become apparent from the following detailed description taken with the accompanying drawings. It is noteworthy that the drawings are intended for illustrating the present invention only, but not for limiting the scope of the invention, and the drawings are not necessarily drawn according to the actual shape, size or proportion of the device.

Figure 1:
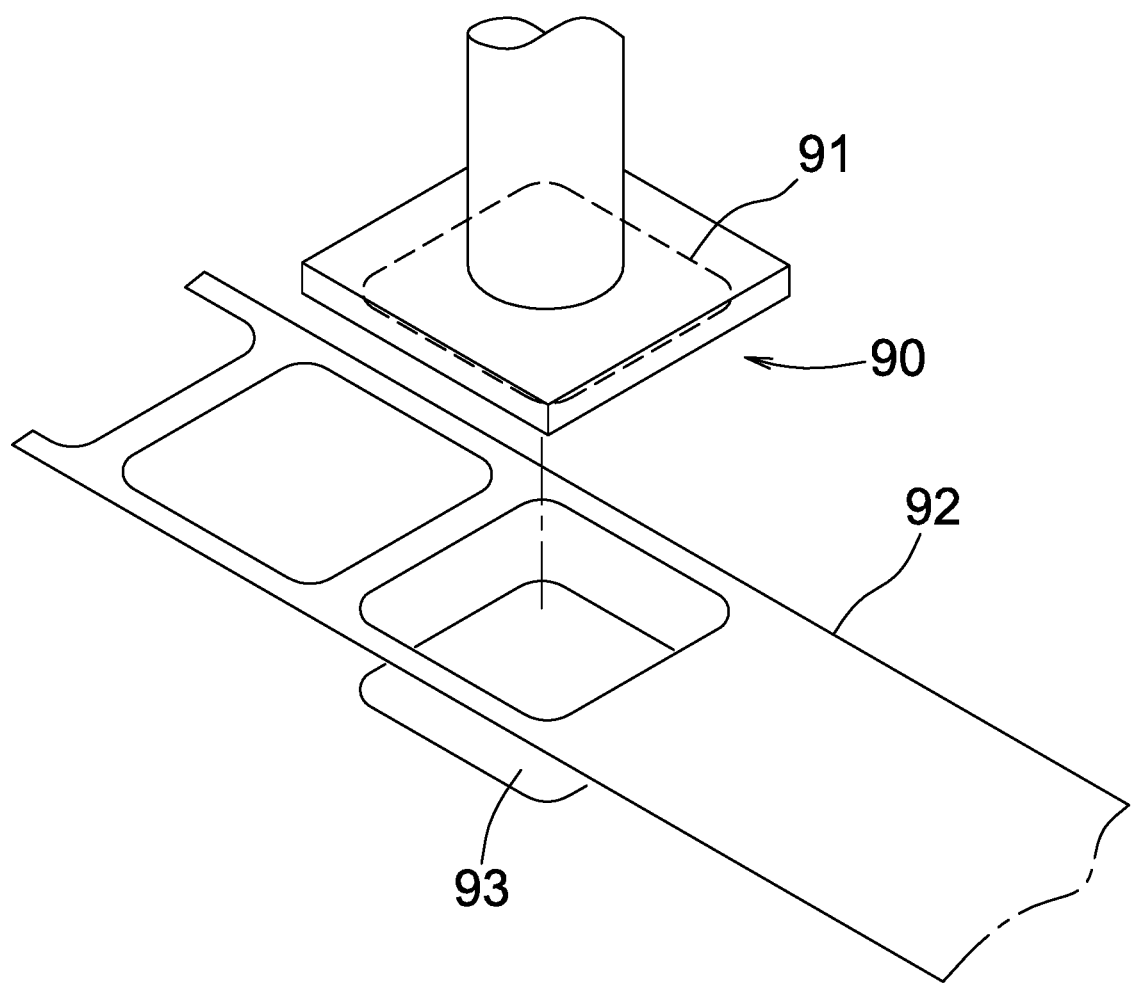
FIG. 1 is a schematic view of a shape cutting assembly of a conventional electrode patch.
Figure 1A:
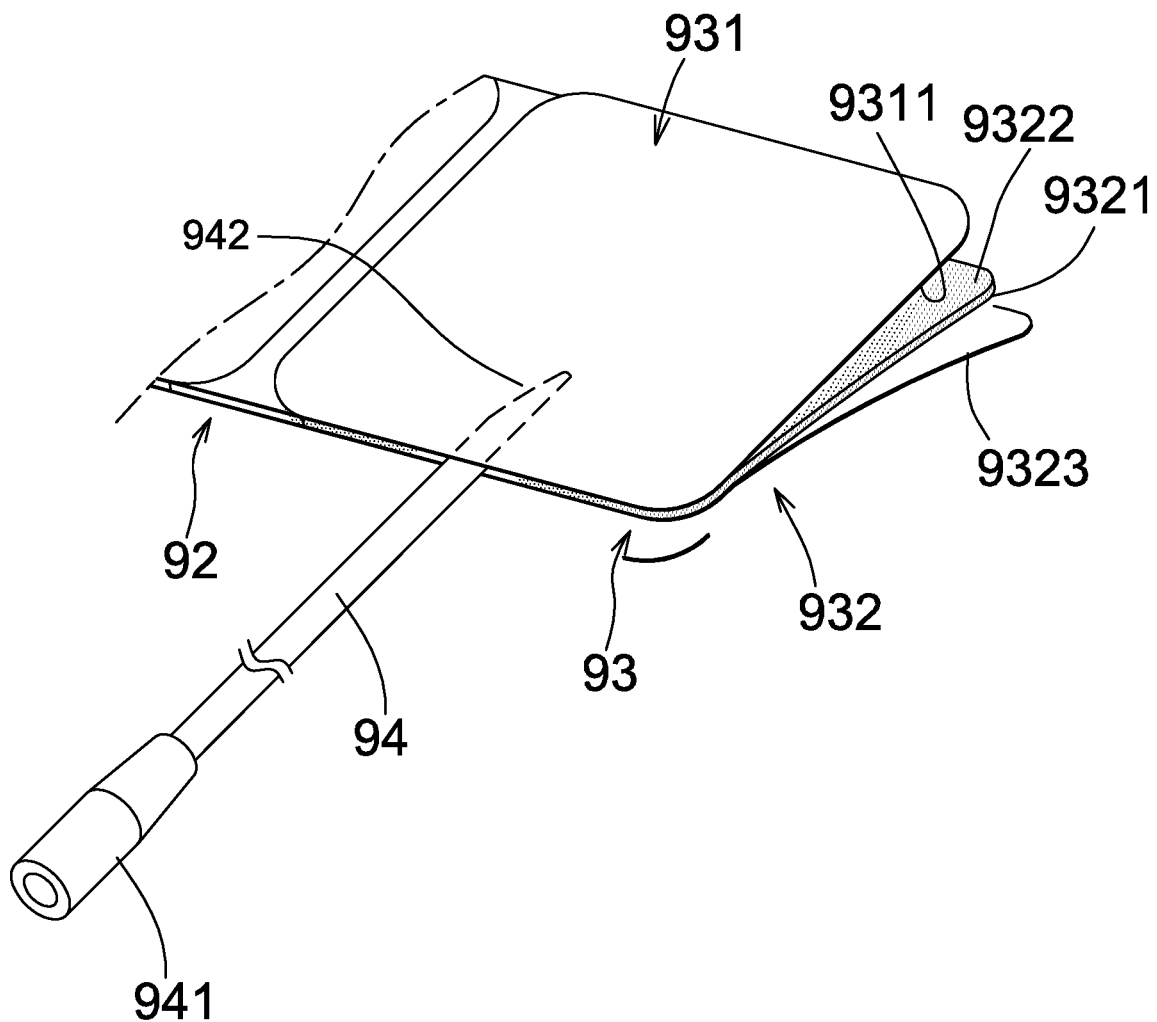
FIG. 1a is a schematic view of an electrode lead of a conventional electrode patch.
Figure 2:
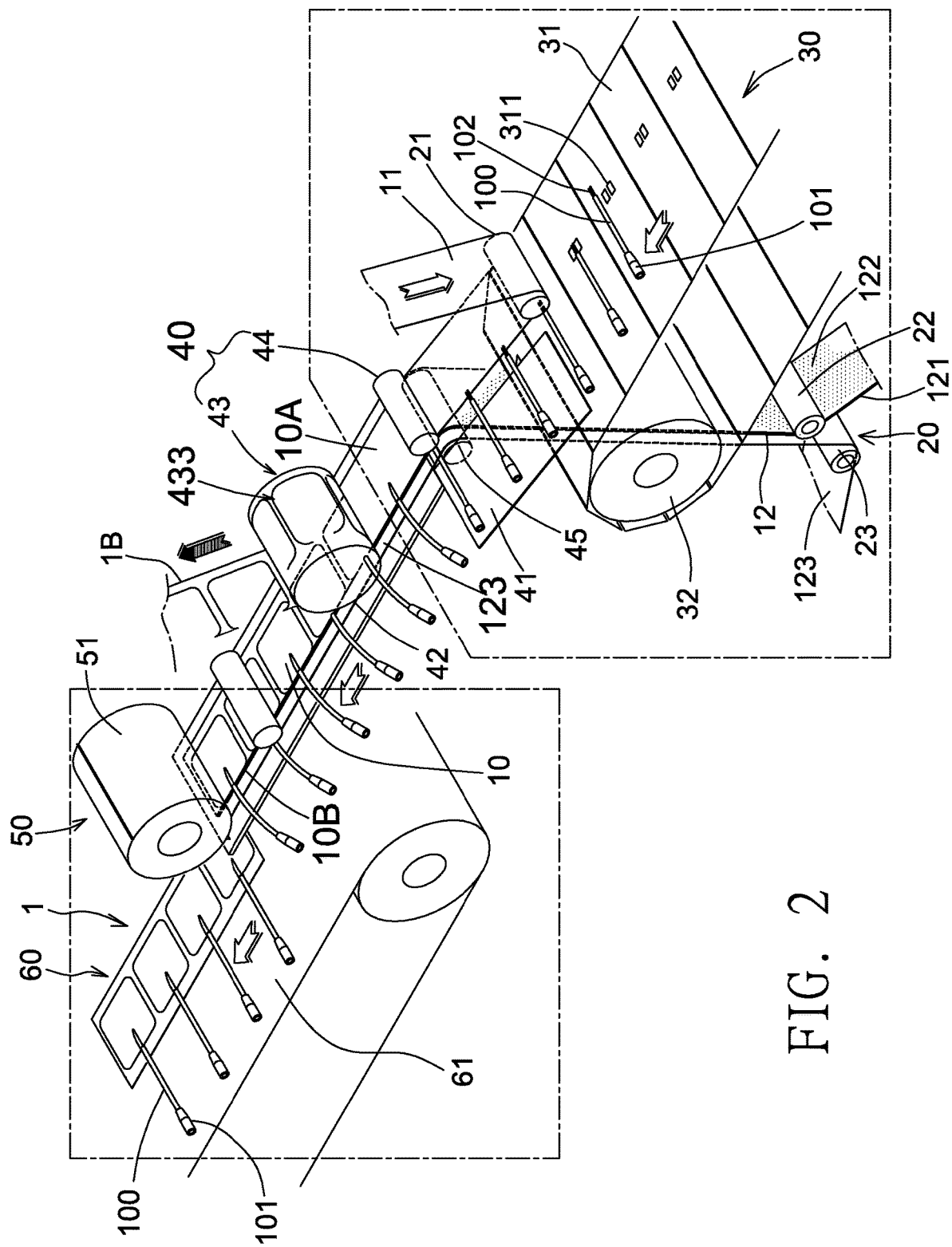
FIG. 2 is a flow chart showing the operation of the present invention.

With reference to FIG. 2 for an electrode patch module 1 produced in a production line by using a shape cutting device of a skin electrode patch of the present invention, the electrode patch module 1 comprises a plurality of electrode patches 10, and production of the present invention the production line comprises a substrate conveyor 20, a positioning conveyor 30, a fitted shape cutting module 40, a section cutting device 50 and a finish products conveying device 60, wherein the substrate conveyor 20 includes a first transmission roller 21 on a side and a second transmission roller 22 and a third transmission roller 23 on the other side. In this embodiment, the first transmission roller 21 is for transmitting a strip coated substrate portion 11 and then transmitting to the positioning conveyor 30; and the second transmission roller 22 and the third transmission roller 23 are provided for transmitting the strip conductive adhesive portion 12 and the release layer 123 respectively, and the conductive adhesive portion 12 is comprised of a glue layer 121 and a conductive layer 122 on the glue layer 121, and the conductive adhesive portion 12 and the release layer 123 are attached during the transmission, and then the conductive adhesive portion 12 with the attached release layer 123 is transmitted to a pressing wheel 45 of a fitted shape cutting module 40. In addition, the coated substrate portion 11 and the conductive adhesive portion 12 are not limited to the aforementioned assembly only.

The positioning conveyor 30 includes a conveyor belt 31 and a transmission wheel 32 disposed at both ends of the conveyor belt 31 respectively. In this embodiment, the conveyor belt is operable in a loop, and the transmission wheel 32 is provided for supplying the power for moving the conveyor belt 31 in a loop, and the conveyor belt 31 has a plurality of positioning tools 311 installed thereon, and the positioning tool 311 is for positioning an electrode lead 100, and both ends of the electrode lead 100 have a conductive wire connector 101 and an electrode terminal 102. During the assembling and use of the positioning conveyor 30, the positioning tool 311 is provided for positioning the electrode lead 100. In this embodiment, the electrode terminal 102 is embedded and positioned by the positioning tool 311, so that the electrode lead 100 is positioned onto the conveyor belt 31 and moved and conveyed accordingly.

The fitted shape cutting module 40 is installed in the successive portion of the positioning conveyor 30 and includes a stripping guide plate 41, a pressing wheel 44, 45, a carrying plate 42 and a shape cutting unit 43, and the stripping guide plate 41 is slantingly coupled to an end portion of the positioning conveyor 30, and the front end of the stripping guide plate 41 is configured to be corresponsive to the first transmission roller 21 for transmitting the coated substrate portion 11. In the meantime, the first transmission roller 21 is also disposed in the rear upper portion of the conveyor belt 31, and the pressing wheels 44, 45 are installed in the successive portion of the stripping guide plate 41, the conductive adhesive portion 12 and the coated substrate portion 11 have equivalent or equal widths, and the conductive adhesive portion 12 is transmitted through the pressing wheel 45 to the fitted shape cutting module 40, and the pressing wheels 44, 45 are provided for pressing the conductive adhesive portion 12 and the coated substrate portion 11 into a strip to form the electrode strip 10A, and the release layer 123 is combined with the bottom of the electrode strip 10A, and the release layer 123 is wider and slightly protruded from the electrode strip 10A, so that a combination of the electrode strip 10A formed on the carrying plate 42 and the release layer 123 are to be cut into a strip assembly, and the carrying plate 42 is installed in the successive portion of the pressing wheels 44, 45, and the shape cutting unit 43 is installed above an appropriate position of the carrying plate 42.

Figure 3:
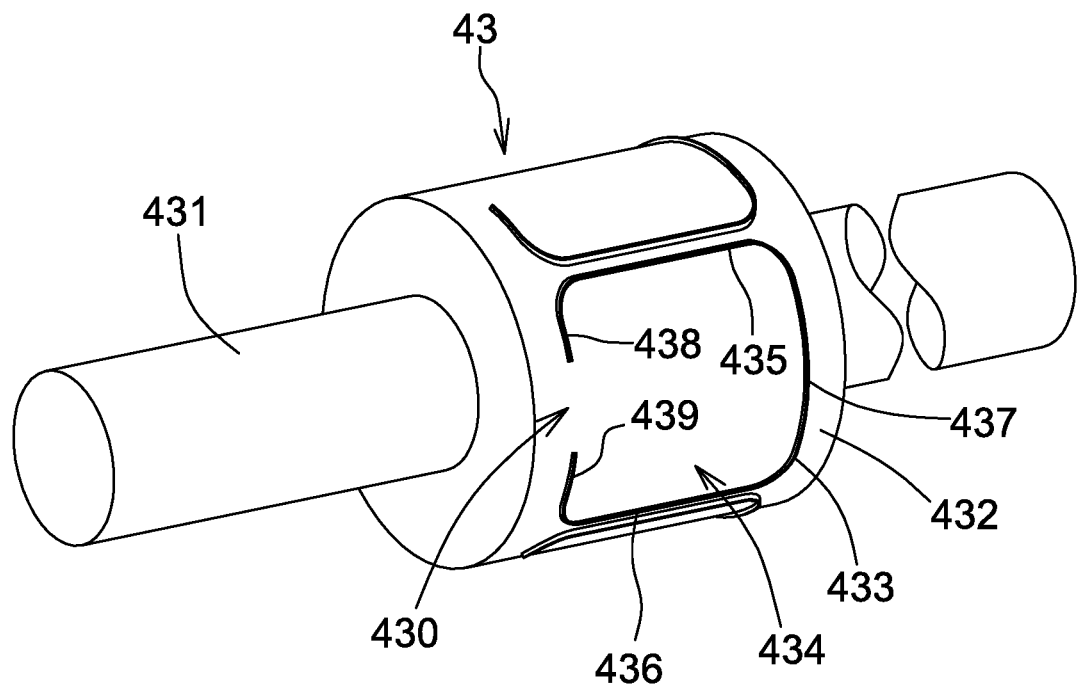
FIG. 3 is a perspective view of a shape cutting unit of the present invention.
Figure 4:
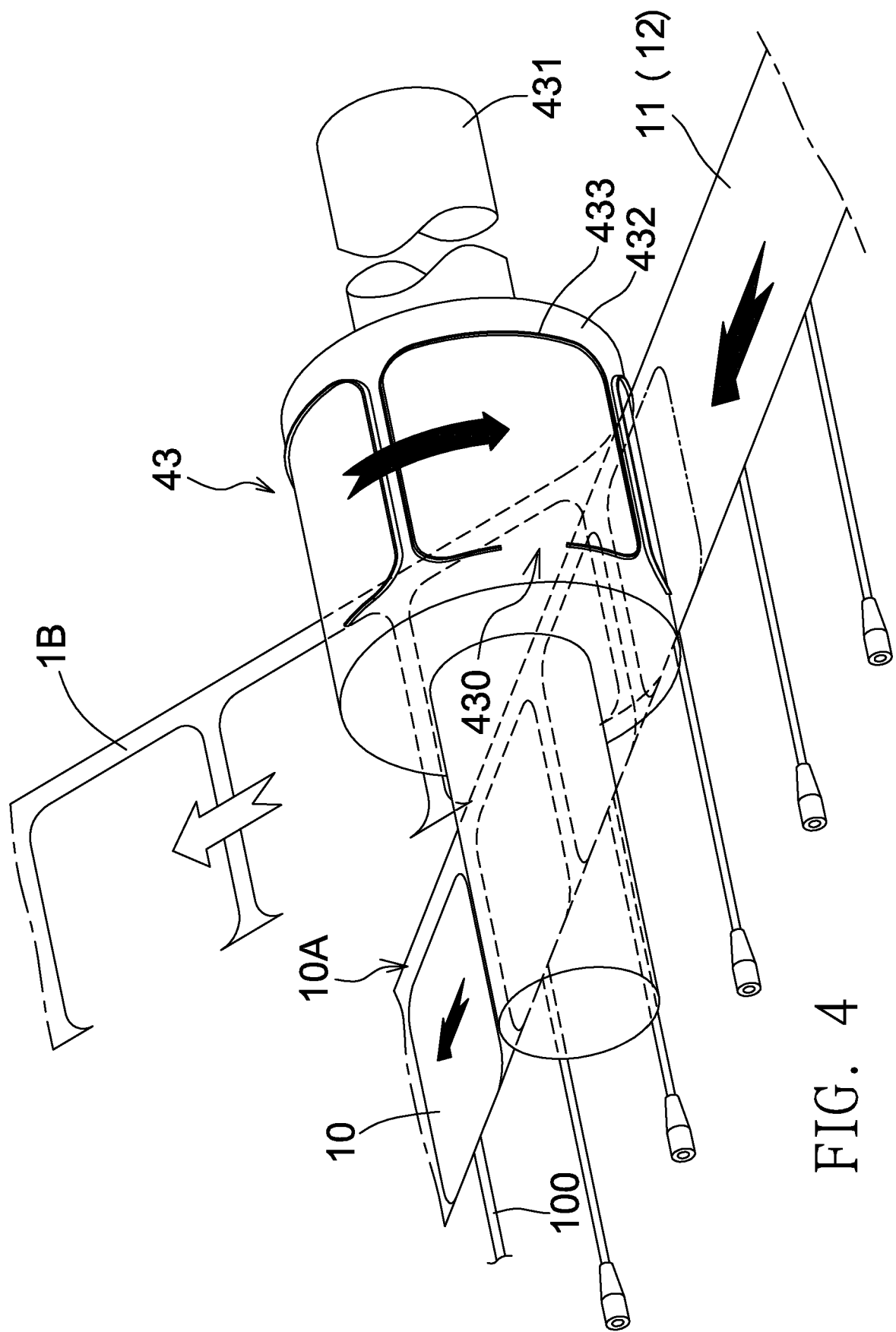
FIG. 4 is a perspective view showing a shape cutting operation of a shape cutting unit of the present invention.

In FIGS. 3 and 4, the shape cutting unit 43 comprises a driving shaft 431 and a roller body 432, and the driving shaft 431 is a rotatable transmission shaft for linking and rotating the roller body 432, and the roller body 432 has a plurality of cutting knives 433, and the cutting knifes 433 are substantially in a geometrical shape and includes two protruding side cutters 435, 436 and a first-end cutter 437 at an axial end, and opposite ends of the first-end cutter 437 have a second-end cutter 438, 439, wherein the first-end cutter 437 is coupled to the side cutters 435, 436 on both sides (connected at an arc end corner), and the side cutter 435 and the second-end cutter 438, and the side cutter 436 and the second-end cutter 439 are coupled respectively (connected at an arc end corner) to enclose and form a shape cutting area 434 inside the cutting knife 433, and a gap 430 is formed between the second-end cutter 438, 439, and the gap 430 does not have the installation of the cutting knife 433.

Figure 3A:
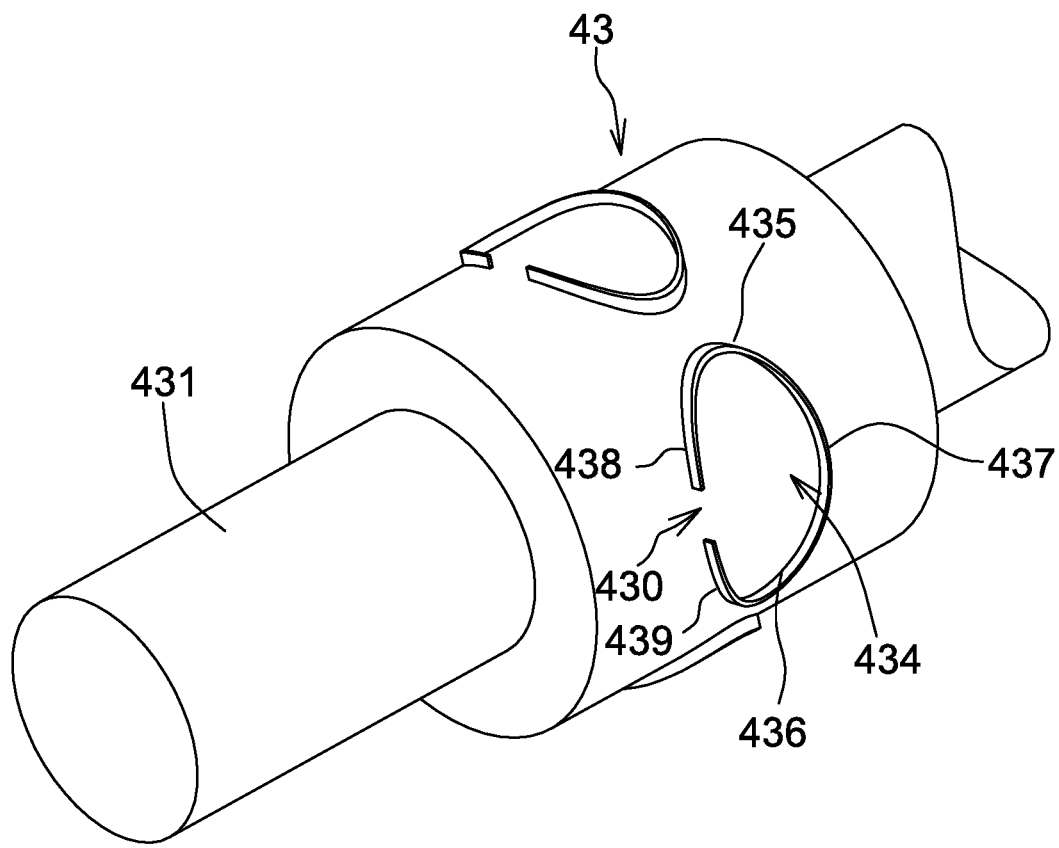
FIG. 3a is a perspective view of a shape cutting unit of another embodiment of the present invention.

The cutting knife 433 is a substantially square or rectangular assembly. In other embodiment, the cutting knife 433 is a geometrical shaped assembly (as shown in FIG. 3a), and the arc geometrical shape includes but not limited to a circular, elliptical or egg shape, and the geometrical shaped cutting knife 433 also has a gap, and the gap may be the gap 430. In other words, the central portion of the first-end cutter 437 of the cutting knife 433 forms an end of the arc shaped cutting knife 433, and both sides of the side cutters 435, 436, the second-end cutters 438, 439 and the first-end cutter 437 form two side edges of the arc shaped cutting knife 433, and the gap 430 forms the other end gap of the arc shaped cutting knife 433, and the gap 430 does not have the installation of the cutting knife 433.

The section cutting device 50 is installed at the rear portion of the fitted shape cutting module 40, and the section cutting device 50 includes a section cutting wheel 51. The finish products conveying device 60 is installed at the successive portion of the section cutting device 50, and the finish products conveying device 60 includes a conveying portion 61.

In an application of shape cutting device of a skin electrode patch of the present invention, the coated substrate portion 11 is pulled backward by a pulling force, and the coated substrate portion 11 finally enters into the rear upper portion of the conveyor belt 31 from the first transmission roller 21, so that the electrode lead 100 pre-installed on the conveyor belt 31 is attached onto a glue layer of the coated substrate portion 11 (not shown in the figure), and then moved together with the coated substrate portion 11. In this embodiment, the electrode terminal 102 of the electrode lead 100 is adhered to the coated substrate portion 11 (or the glue layer) and then the coated substrate portion 11 is entered into the stripping guide plate 41 and continuously moved further. When the coated substrate portion 11 is moved to the pressing wheels 44, 45, it is attached to the conductive adhesive portion 12 having the release layer 123 attached below. The conductive adhesive portion 12 is also pulled backward by a pulling force, and the conductive adhesive portion 12 is finally entered from the pressing wheel 45 into the carrying plate 42. Since the coated substrate portion 11 and the conductive adhesive portion 12 are entered into the carrying plate 42 of the fitted shape cutting module 40 through the pressing wheel 44, 45, so that the coated substrate portion 11 and the conductive adhesive portion 12 are laminated and adhered with each other by the pressing wheels 44, 45 to produce the electrode strip 10A. Now, the electrode lead 100 (or the electrode terminal 102) is clamped and positioned between the coated substrate portion 11 and the conductive adhesive portion 12. In other words, the electrode strip 10A together with the coated substrate portion 11 completes their adhesion with the conductive adhesive portion 12 and combines with the separately distributed electrode leads 100, and the conductive wire connector 101 is protruded from an outer side of the electrode strip 10A. In this embodiment, the electrode terminal 102 of the electrode lead 100 is clamped and positioned in the electrode strip 10A (including the coated substrate portion 11 and the conductive adhesive portion 12), and the conductive wire connector 101 of the electrode lead 100 is protruded from an outer side of the electrode strip 10A. Now, the electrode lead 100 (or electrode terminal 102) is clamped and positioned between the coated substrate portion 11 and the conductive adhesive portion 12, and the conductive wire connector 101 is protruded out from the outside of the coated substrate portion 11 and the conductive adhesive portion 12. In this embodiment, the electrode terminal 102 of the conductive wire connector 101 is clamped and positioned between the coated substrate portion 11 and the conductive adhesive portion 12, and the remaining ones are protruded out from the outer side of the coated substrate portion 11 and the conductive adhesive portion 12.

Figure 5:
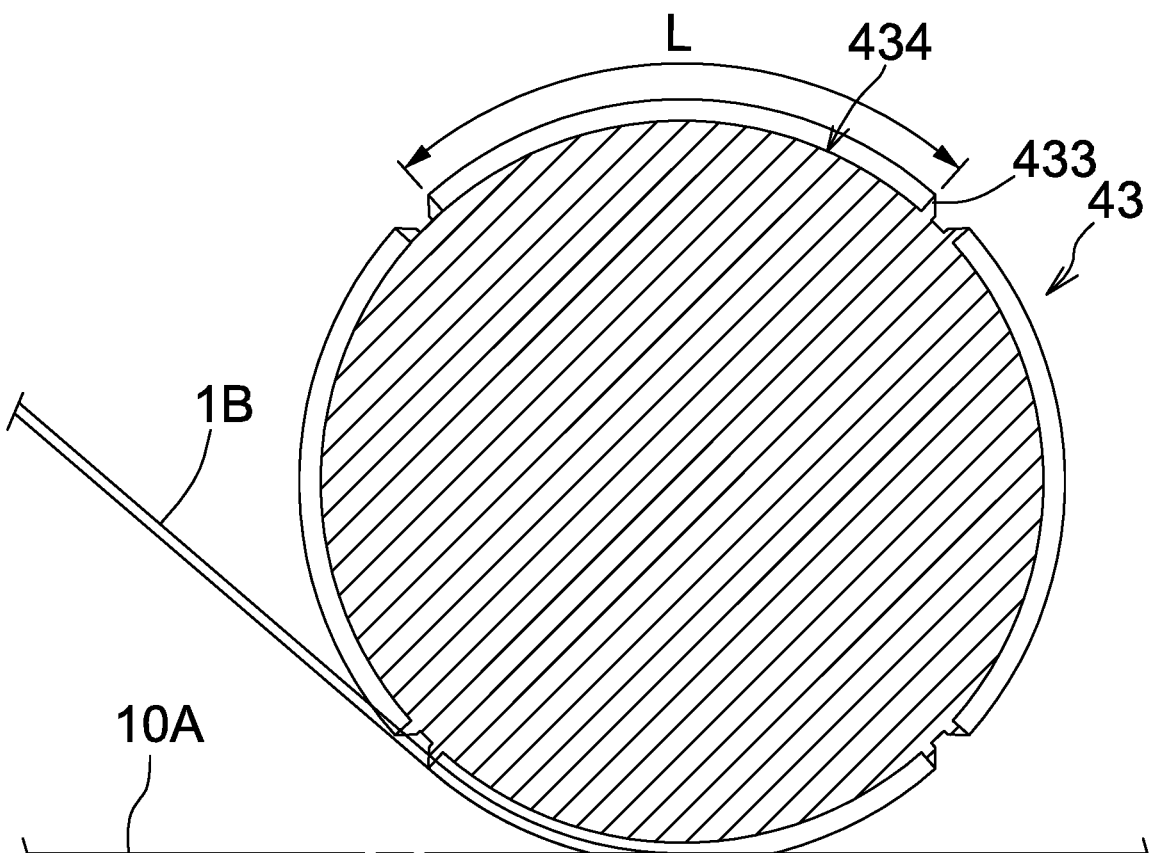
FIG. 5 is a cross-sectional view showing a shape cutting operation of a shape cutting unit of the present invention.
Figure 6:
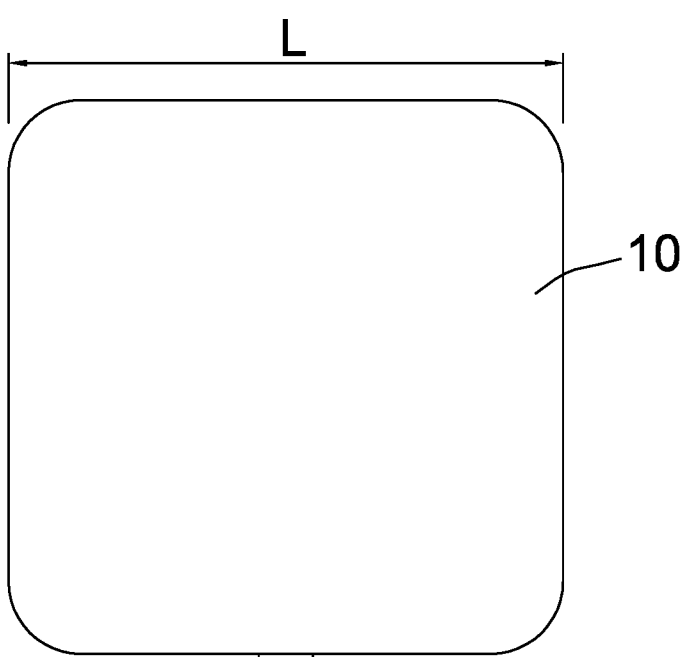
FIG. 6 is a schematic view of an electrode patch of the present invention after the shape cutting.

With reference to FIGS. 5 and 6, the electrode strip 10A (including the adhesive strips of the coated substrate portion 11 and the conductive adhesive portion 12) clamped and secured to the electrode lead 100 is moved at the carrying plate 42. When the electrode strip 10A passes through the shape cutting unit 43, the electrode strip 10A is cut by the cutting knife 433, but the release layer 123 combined with the bottom of the electrode strip 10A is not cut by the cutting knife 433, and the release layer 123 maintains its integrity, and the second-end cutters 438, 439 are aligned precisely with or slightly protruded from a strip edge 10B of the electrode strip 10A, and the strip edge 10B is disposed on a side of the electrode strip 10A where the electrode leads 100 are protruding. In this embodiment, the cutting knife 433 has a wheel width L (which is the length between the two side cutters 435, 436), and the cut electrode patch 10 has a width equal to L, and the second-end cutters 438, 439 are substantially disposed at edges of the attached body, and the gap 430 is provided for preventing the electrode lead 100 from being cut or broken unintentionally, and a remaining material strip 1B of the attached body after the cutting is separated. After the shape cutting, the electrode strip 10A is transmitted through the section cutting device 50 and cut by the section cutting wheel 51, such that the attached body of the strip coated substrate portion 11 and conductive adhesive portion 12 becomes a strip attached body, so as to form the electrode patch module 1. The electrode patch module 1 falls on the conveying portion 61 of the finish products conveying device 60, and the finish product is collected.

Figure 7:
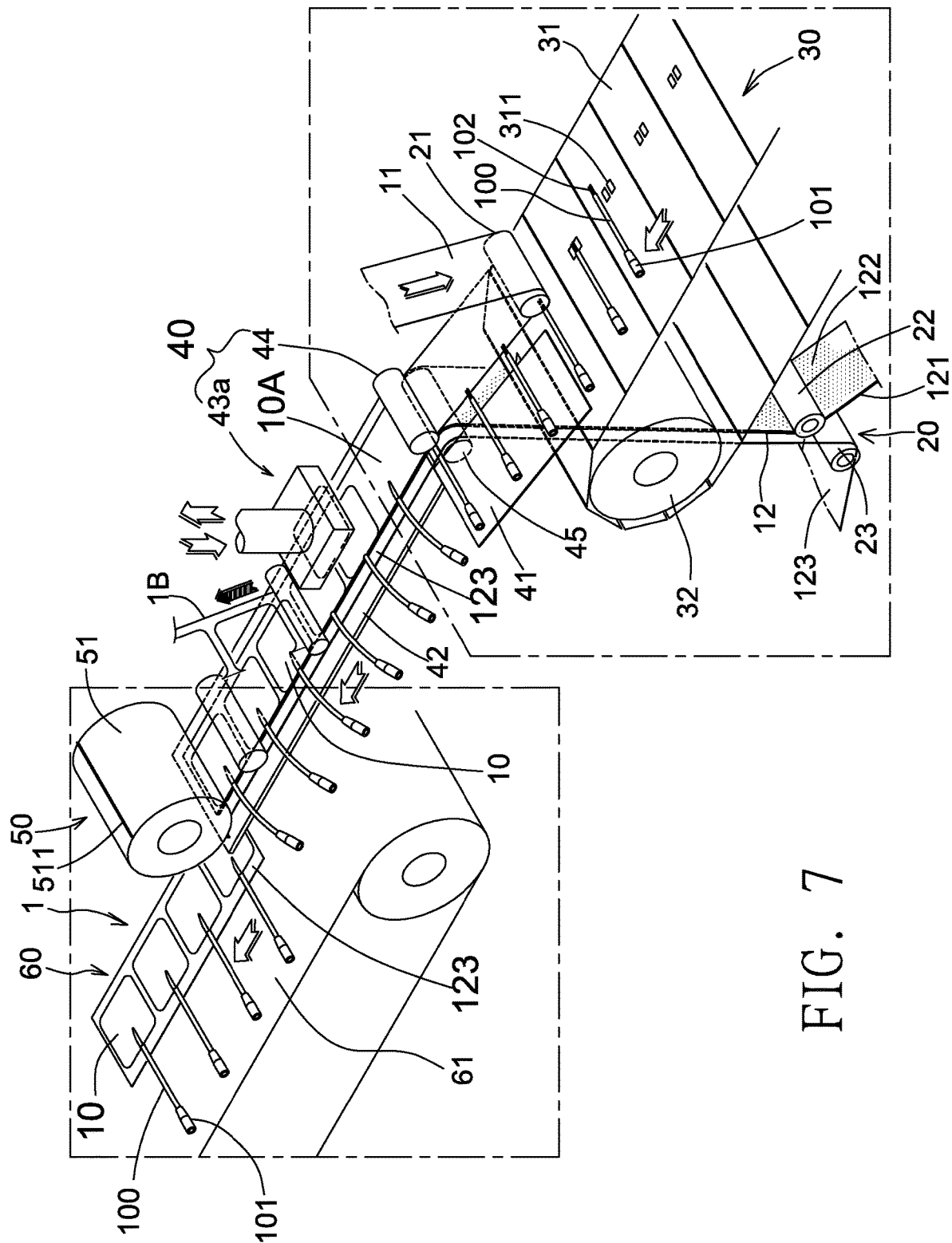
FIG. 7 is a flow chart of an operation in accordance with a first implementation mode of the present invention.
Figure 8A:
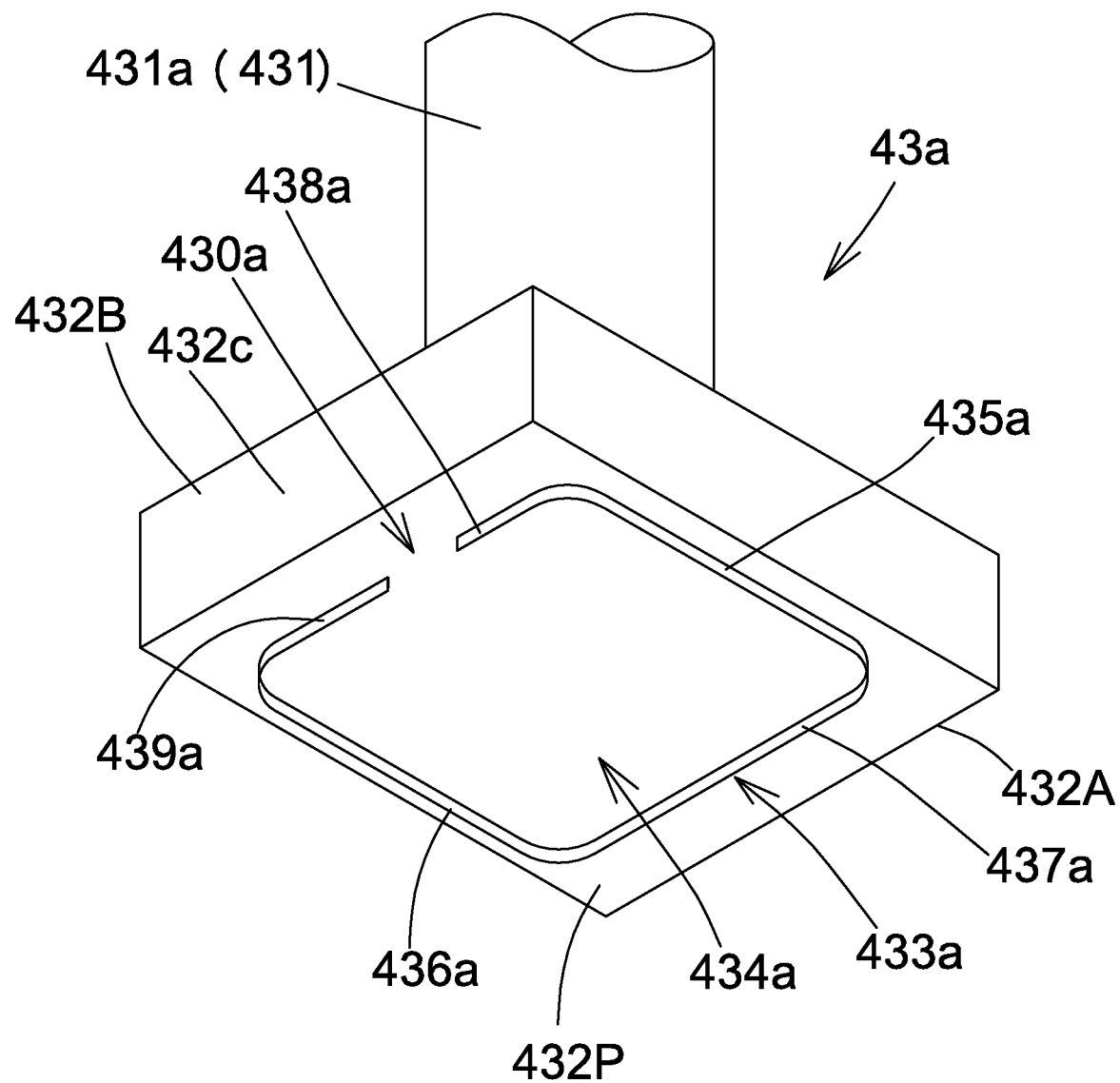
FIG. 8a is a schematic view of a shape cutting unit in accordance with the first implementation mode of the present invention.

With reference to FIGS. 7 and 8a for a shape cutting unit 43a in accordance with the first implementation mode of the present invention, the shape cutting unit 43a comprises a driving shaft 431 and a cutting tool holder 432c coupled to each other, and the driving shaft 431 is a stamping shaft 431a, and the cutting tool holder 432c has a horizontal cutting tool surface 432P, and a cutting knife 433a is installed on the cutting tool surface 432P, and the cutting knife 433a is in a geometric shape, and the stamping shaft 431a is coupled to a stamping machine (not shown in the figure), and the stamping machine drives the stamping shaft 431a to move up and down quickly and repetitively, so that the cutting knife 433a can carry out a fast cutting. The cutting knife 433a comprises two protruding side cutters 435a, 436a and a first-end cutter 437a, and the first-end cutter 437a is disposed adjacent to an end of the cutting tool holder 432c (such as the cutting tool holder end 432A as shown in the figures), and the first-end cutter 437a has at least two opposite ends, and the two opposite ends are adjacent to the other end of the cutting tool holder 432c (such as the cutting tool holder end 432B as shown in the figures), and each opposite end of the first-end cutter 437a has a second-end cutter 438a, 439a, and the first-end cutter 437a is coupled to the side cutters 435a, 436a on both sides, and the two side cutters 435a, 436a are coupled to the two second-end cutters 438a, 439a respectively. In other words, the side cutter 435a is coupled to the second-end cutter 438a (through a connection with a fillet or an arc-end angle), and the side cutter 436a is coupled to the second-end cutter 439a (through a connection with a fillet or an arc-end angle), and the first-end cutter 437a, the two side cutters 435a, 436a and the two second-end cutters 438a, 439a are enclosed to form a cutting area 434a inside the cutting knife 433a, and only one gap 430a is formed between two second-end cutters 438a, 439a of the cutting knife 433a, and the gap 430a is disposed at a non-contact position of the two second-end cutters 438a, 439a. In other words, the gap 430a does not have the installation of the cutting knife 433a. Wherein, the cutting knife 433a is continuous and complete from the second-end cutter 438a to another second-end cutter 439a or from the second-end cutter 439a to another second-end cutter 438a, and the gap 430a is provided for preventing the electrode lead 100 from being cut off during the stamping and cutting processes.

Figure 8B:
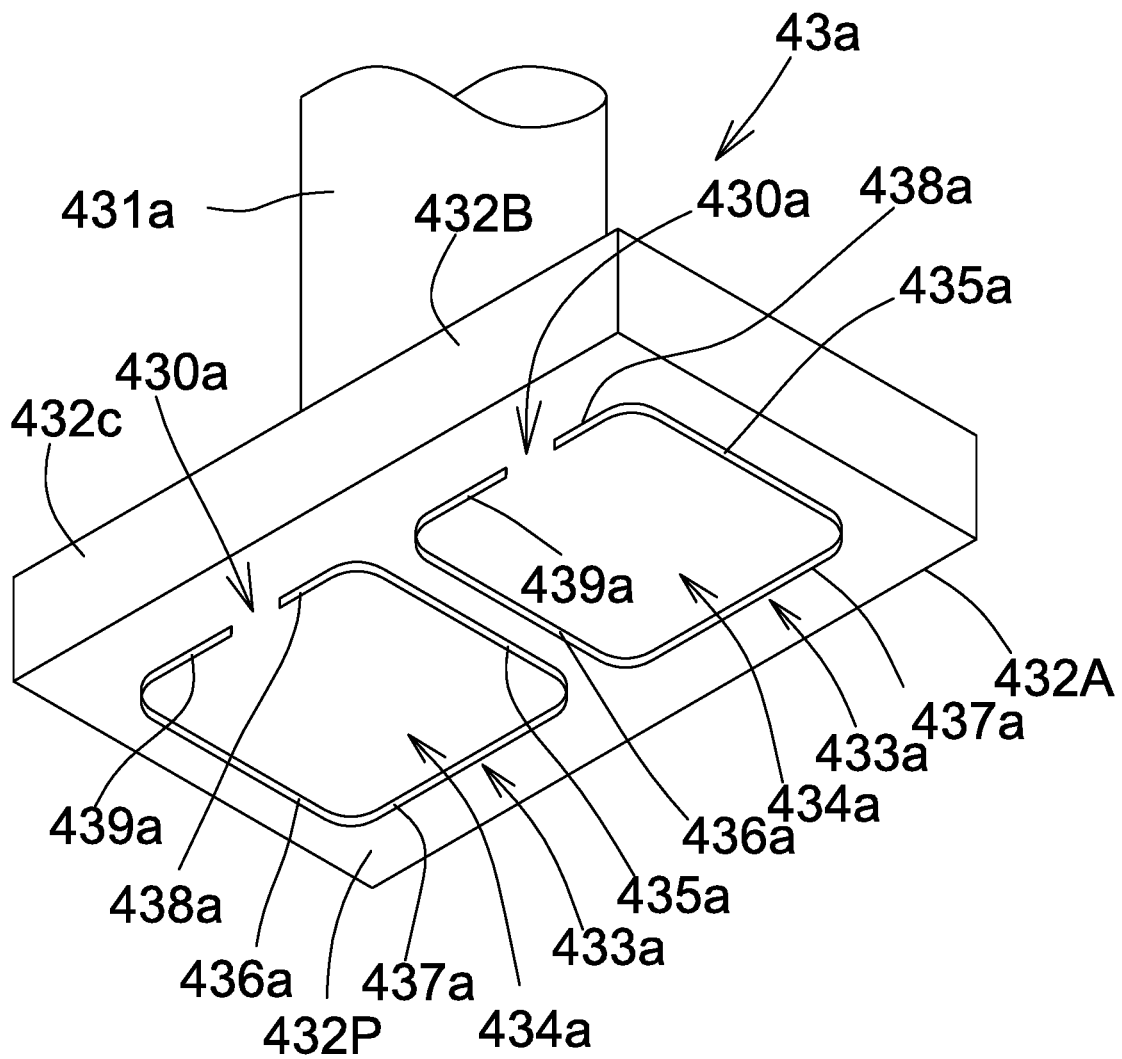
FIG. 8b is a schematic view of a plurality of shape cutting units in accordance with the first implementation mode of the present invention.

With reference to FIG. 8b for the schematic view of a shape cutting unit 43a installed with a plurality of cutting knives 433a in accordance with the first implementation mode of the present invention, the cutting tool surface 432P of the cutting tool holder 432c has two cutting knives 433a, but the quantity of cutting knives 433a is not limited. The assembly of the cutting knife 433a is the same as that shown in FIG. 8a, and thus its description will not be repeated. In this implementation mode, the cutting knife 433a is substantially in a square shape, a rectangular shape, or any other geometric shape, and the cutting knives 433a in these geometric shapes have the configuration of the fillet and the gap 430a.

Figure 8C:
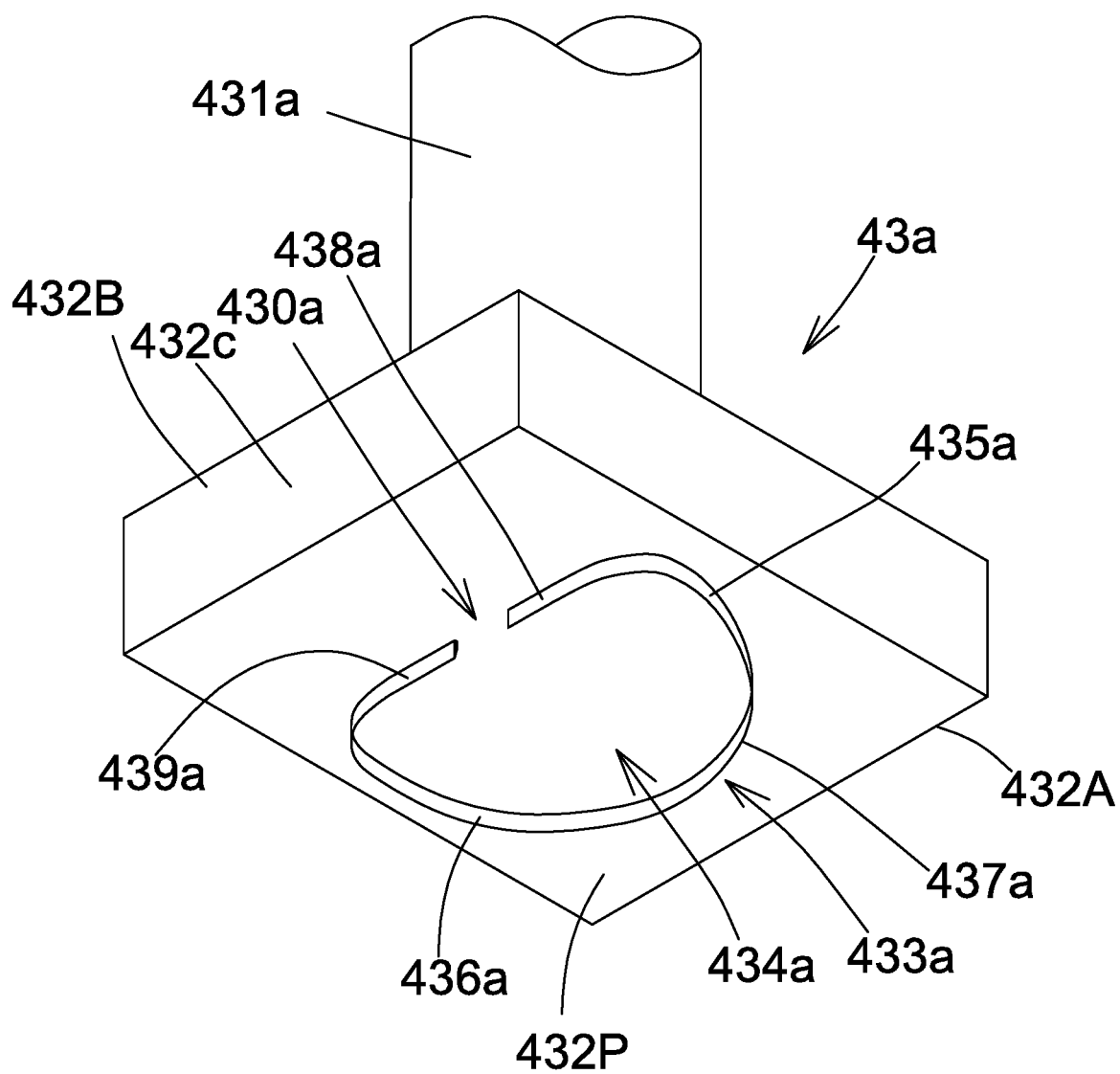
FIG. 8c is a schematic view of a shape cutting unit in accordance with a second implementation mode of the present invention.

With reference to FIG. 8c for a shape cutting unit 43a in accordance with the second implementation mode of the present invention, the shape cutting unit 43a is modified based on the structure of the first embodiment, and the difference resides on that the cutting knife 433a is in a geometric arc shape, which is a circular shape, an elliptical shape, or an egg shape. In other words, the central position of the first-end cutter 437a of the cutting knife 433a is formed into the geometric arc shape to constitute an end of the cutting knife 433a, and the side cutters 435a, 436a, the second-end cutters 438a, 439a and both sides of the first-end cutter 437a are formed into the geometric arc shape to constitute two side edges of the cutting knife 433a, and the gap 430a is formed into the geometric arc shape to constitute the status of the gap 430a at the other end of the cutting knife 433a. Similarly, the gap 430a does not have the installation of the cutting knife 433a.

Figure 8D:
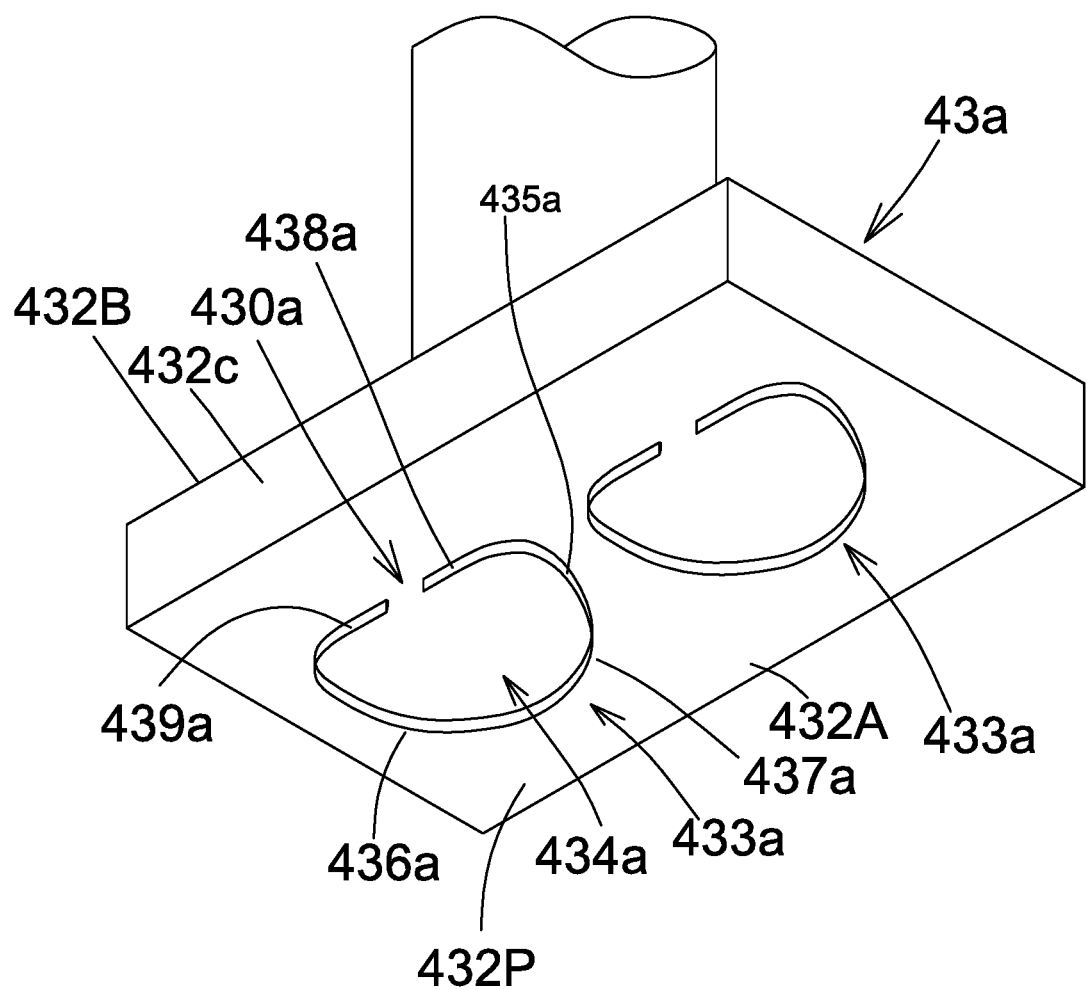
FIG. 8d is a schematic view of a plurality of shape cutting units in accordance with the second implementation mode of the present invention.

With reference to FIG. 8d for a shape cutting unit 43a installed with a plurality of cutting knives 433a in accordance with the second implementation mode of the present invention, two cutting knives 433a are installed on the cutting tool surface 432P of the cutting tool holder 432a, but the quantity of cutting knives 433a is not limited, and the shape of the cutting knife 433a is the same as the shape shown in FIG. 8c, and thus its description will not be repeated.

Figure 9:
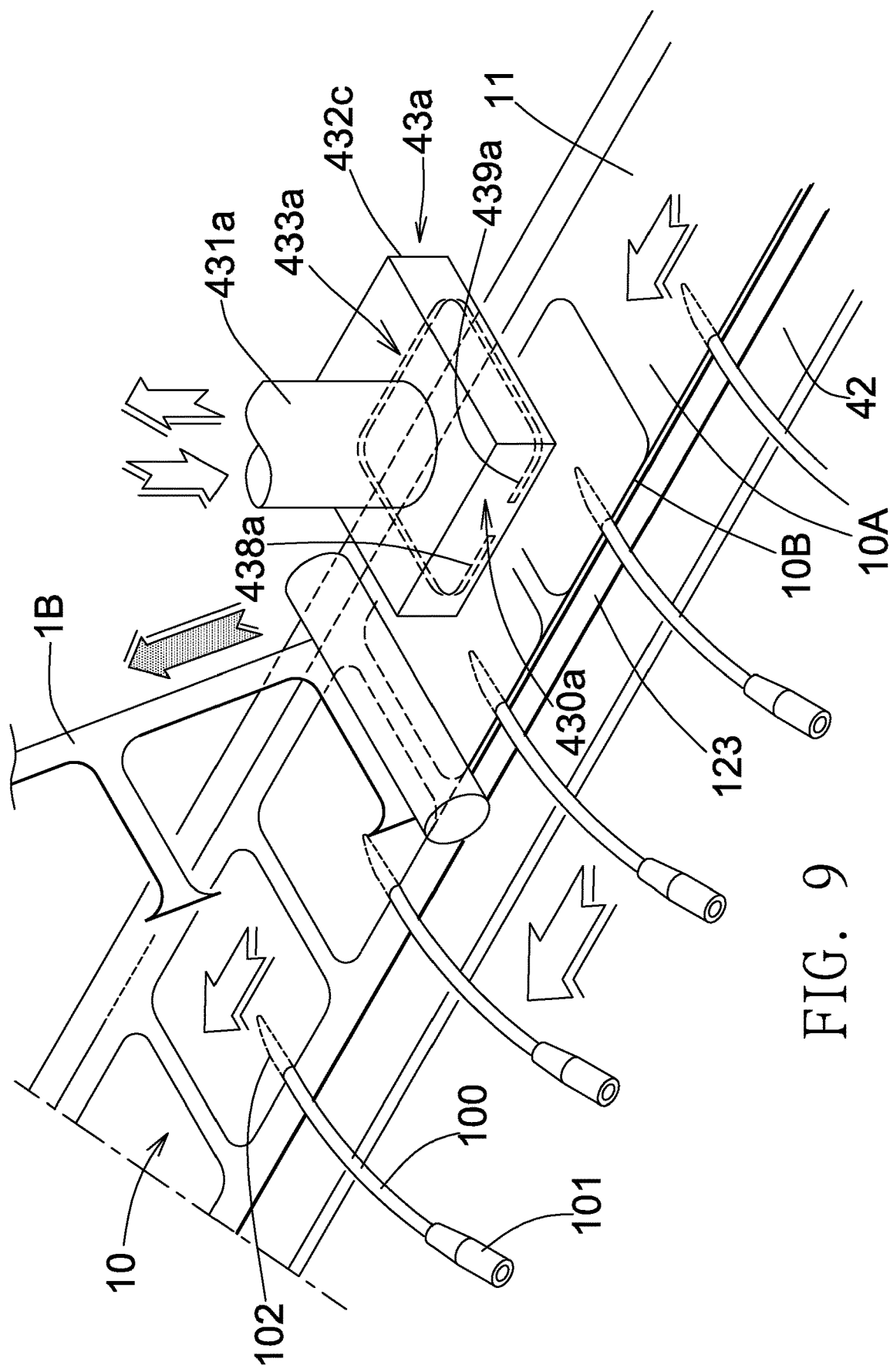
FIG. 9 is a schematic view of a cutting operation of a shape cutting device in accordance with the present invention.

With reference to FIG. 9 for the cutting operation of the shape cutting unit 43, the electrode strip 10A (including the adhesive strips of the coated substrate portion 11 and the conductive adhesive portion 12) clamped and secured with the electrode lead 100 is moved at the carrying plate 42. When the electrode strip 10A passes through the shape cutting unit 43a, the electrode strip 10A is cut by the cutting knife 433a, but the release layer 123 combined with the bottom of electrode strip 10A is not cut by the cutting knife 433a, and the release layer 123 maintains its integrity, and the second-end cutters 438a, 439a are aligned precisely with or slightly protruded from a strip edge 10B of the electrode strip 10A, and the strip edge 10B is disposed on a side of the electrode strip 10A where the electrode leads 100 are protruding. In FIGS. 7 and 9, the second-end cutters 438a, 439b are aligned precisely with the strip edge 10B, and the configuration of the gap 430a can prevent the electrode lead 100 from being cut off. In FIG. 7, the remaining strip 1B after cutting will be separated, so that the electrode patch 10 is formed on the release layer 123. The stamping shaft 431a is coupled to a stamping machine (not shown in the figure), and the stamping machine drives the stamping shaft 431a to move up and down quickly and repetitively, so as to allow the cutting knife 433a to perform a fast cutting. After the cutting, a single-sheet electrode patch 10 will adhere to the release layer 123, and then a wheel cutter 511 of the section cutting wheel 51 of the section cutting device 50 performs the cutting and separating processes, so that the electrode patch groups 1 keep falling onto the conveying portion 61 of the product conveying device 60 for the collection of the products. In the figure, the electrode patch groups 1 are cut into four electrode patches 10 per group by the wheel cutter 511 and adhered onto the cut strip release layer 123, but the quantity of the electrode patches 10 is not limited.

Figure 10A:
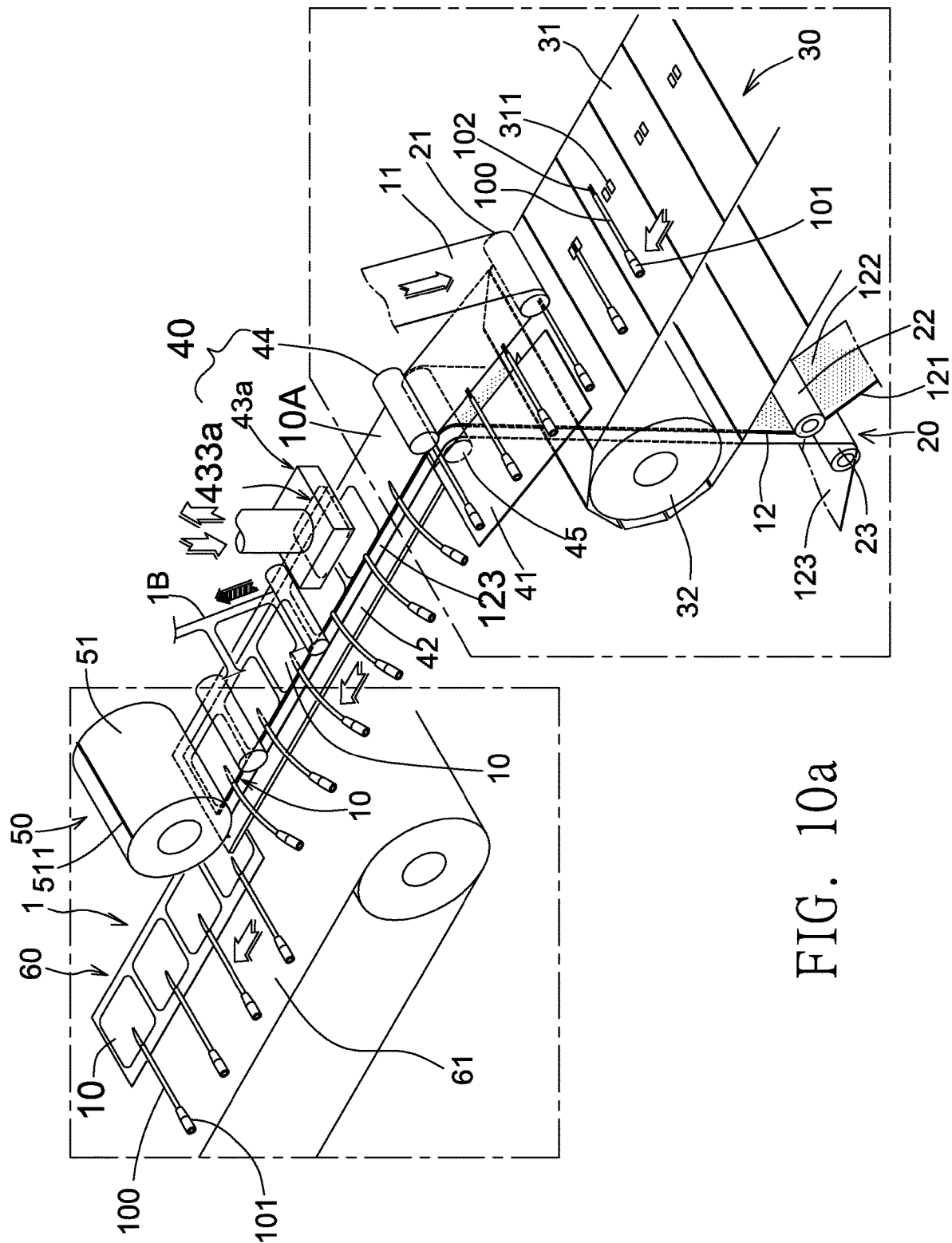
FIG. 10a is a perspective view showing an operation of a shape cutting unit in accordance with a third implementation mode of the present invention.
Figure 10B:
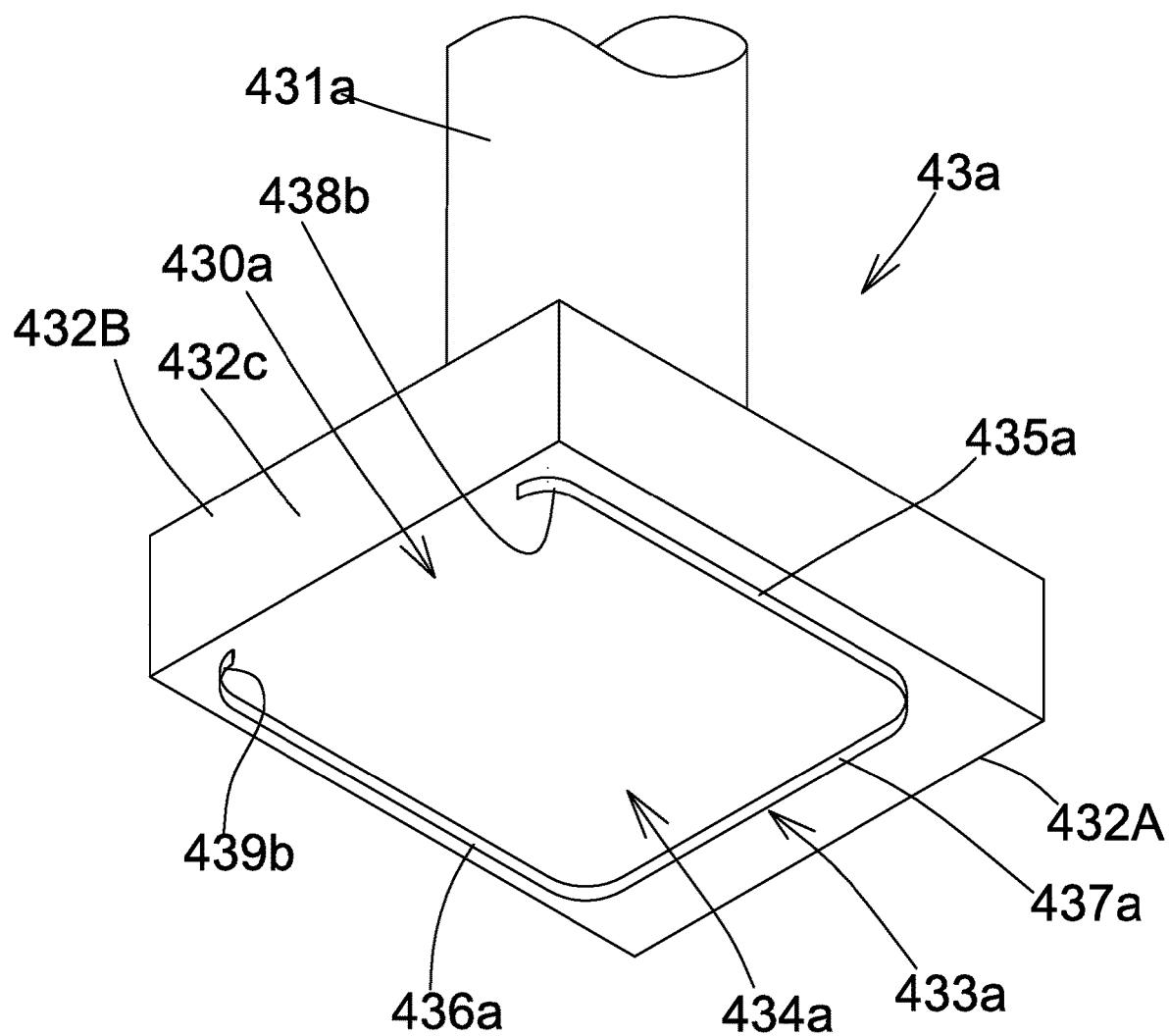
FIG. 10b is a perspective view of a shape cutting unit in accordance with the third implementation mode of the present invention.
Figure 10C:
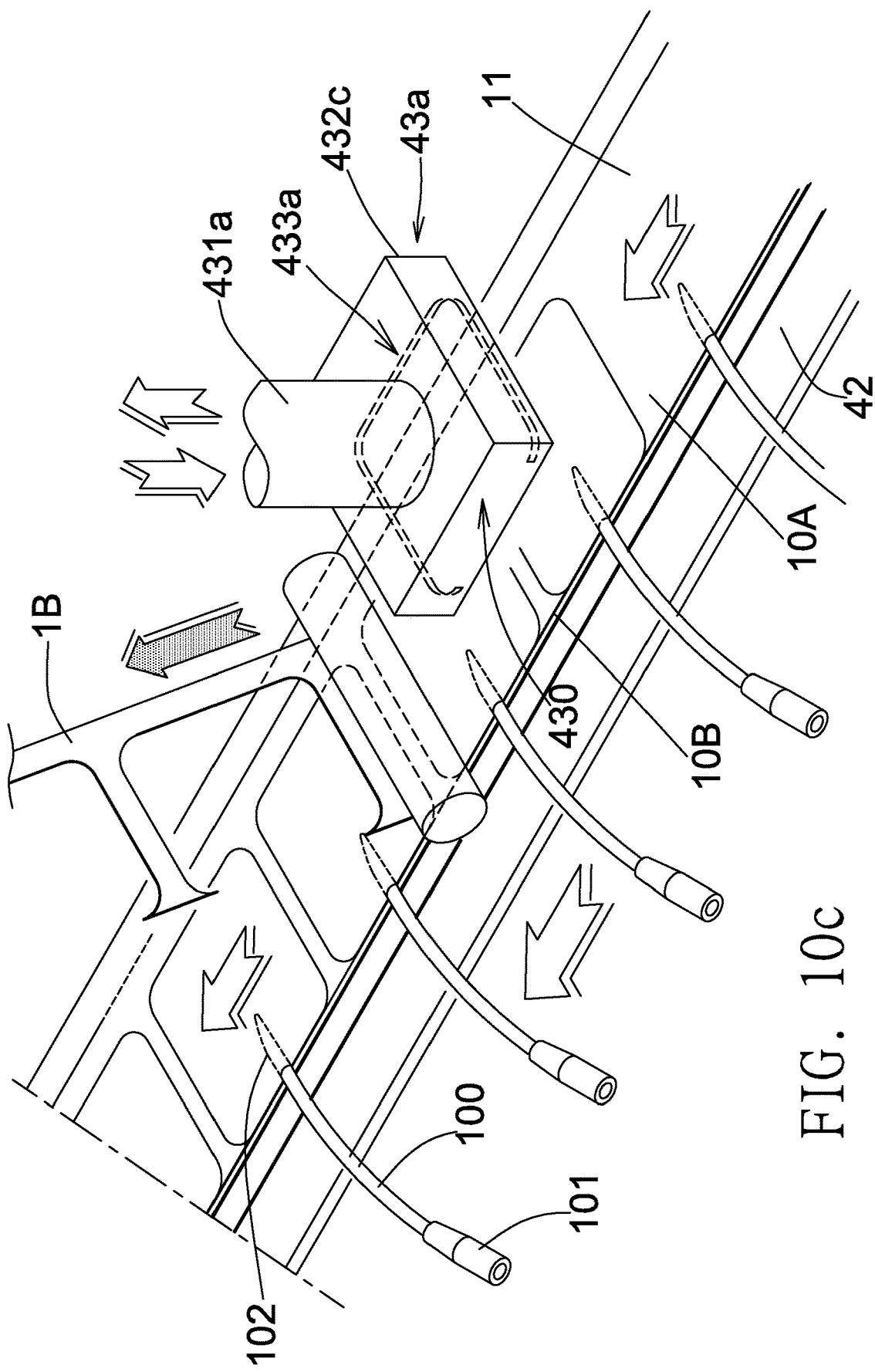
FIG. 10c is a schematic partial view of a cutting operation of a shape cutting unit in accordance with the third implementation mode of the present invention.

With reference to FIGS. 10a, 10b and 10c for a shape cutting unit 43 in accordance with the third implementation mode of the present invention, the shape cutting unit is modified based on the basic structure of the first implementation mode, and their difference resides on that the cutting knife 433a does not have the installation of the second-end cutters 438a, 439a, and an edge of the side cutter 435a, 436a has an end corner cutter 438b, 439b extending inwardly towards the cutting tool holder end 432B with a fillet or an arc-end angle. In other words, the outer side of each opposite end of the first-end cutter 437a has the end corner cutter 438b, 439b, and the end corner cutters 438b, 439b are coupled to the side cutters 435a, 436a respectively, and the gap 430a is formed between the end corner cutters 438b, 439b and provided for preventing the electrode lead 100 from being cut off during the stamping and cutting processes, and the end corner cutter 438b, 439b after the cutting process is configured to be corresponsive to the strip edge 10B of the electrode strip 10A, so as to cut a complete separated electrode patch 10 as well.

Figure 10D:
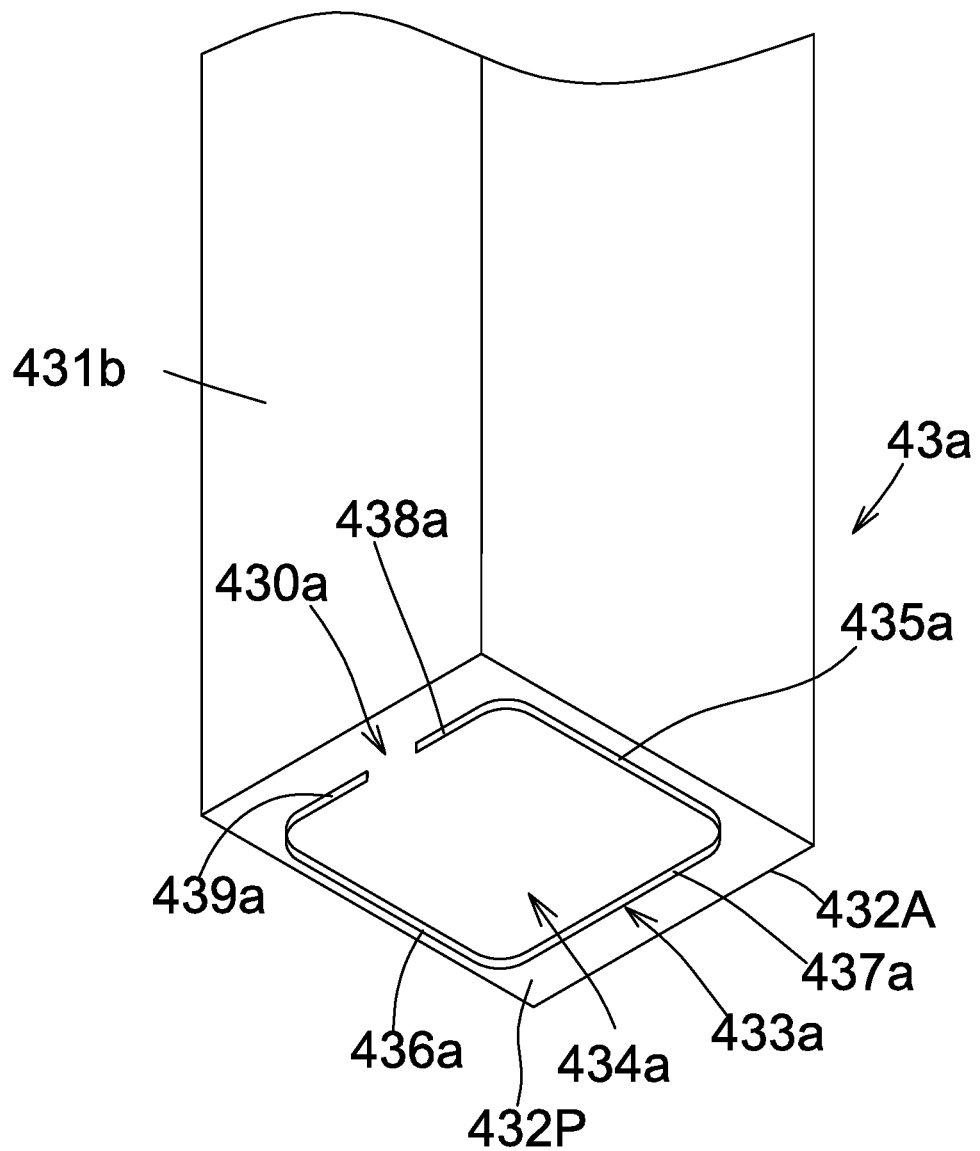
FIG. 10d is a schematic view of a stamping shaft body of a shape cutting unit in accordance with the third implementation mode of the present invention.

With reference to FIG. 10d for a shape cutting unit 43a further comprising a stamping shaft body 431b in addition to the shape cutting units 43a as disclosed in all of the aforementioned embodiments of the present invention, the stamping shaft body 431b is an integral combination of the stamping shaft 431a and the cutting tool holder 432c to achieve the effect of simplifying the components, and the stamping shaft body 431a includes but not limiting to a cylinder, a square column, or any other geometric columns. The stamping shaft body 431b can have the functions of both of the stamping shaft 431a and the cutting tool holder 432c, so that the cutting knife 433a can be installed onto the cutting tool surface 432P of the stamping shaft body 431b directly.

Figure 11:
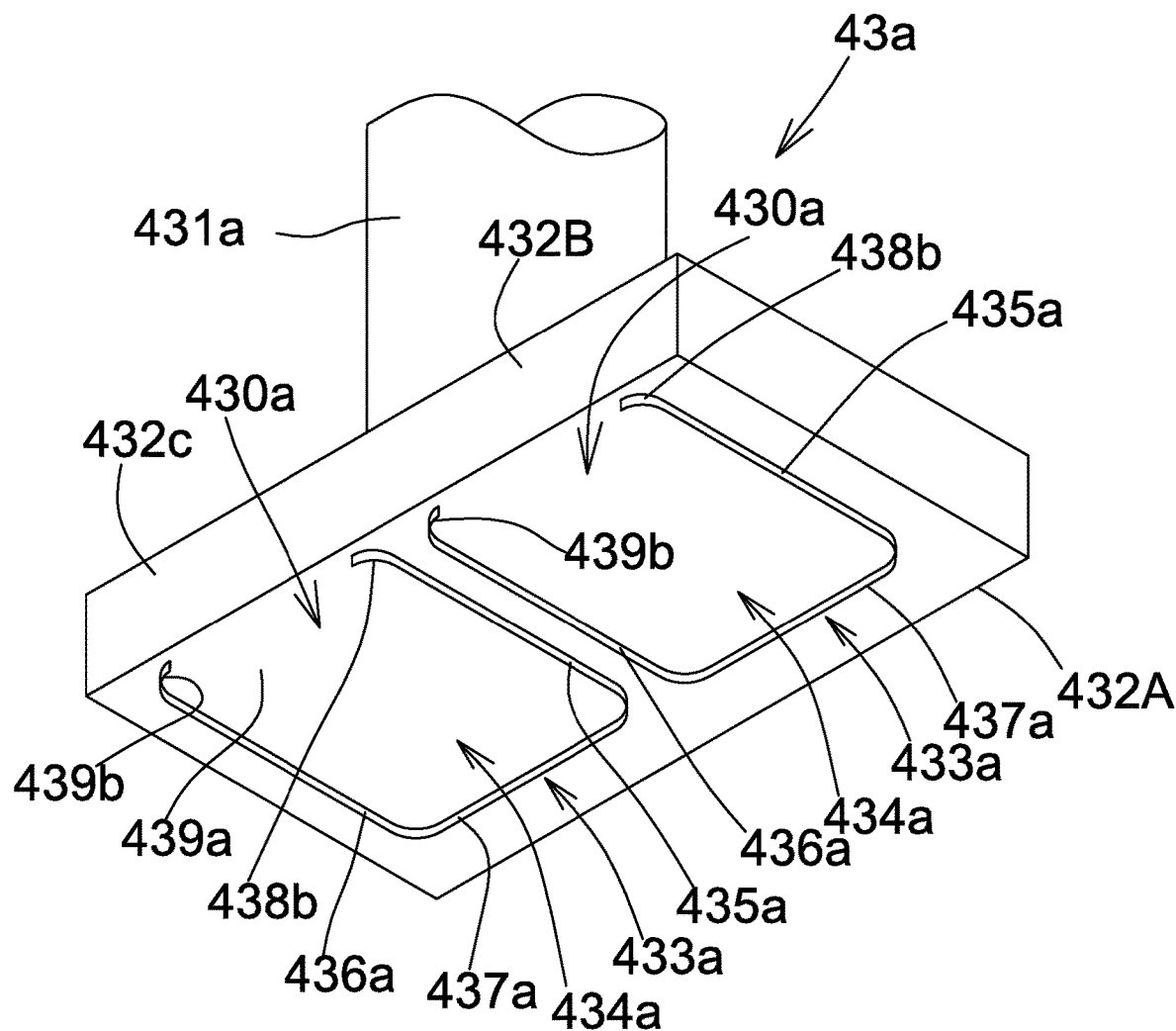
FIG. 11 is a schematic view of installing a shape cutting unit with a plurality of cutting knives in accordance with the third implementation mode of the present invention.

With reference to FIG. 11 for the schematic view of a shape cutting unit 43a installed with a plurality of cutting knives 433a in accordance with the third implementation mode of the present invention, two cutting knives 433a are installed on the cutting tool holder 432c, but the quantity of cutting knives 433a is not limited. The structure of the cutting knife 433a is the same as the structure shown in FIG. 10b, and thus its description will not be repeated.

Figure 12A:
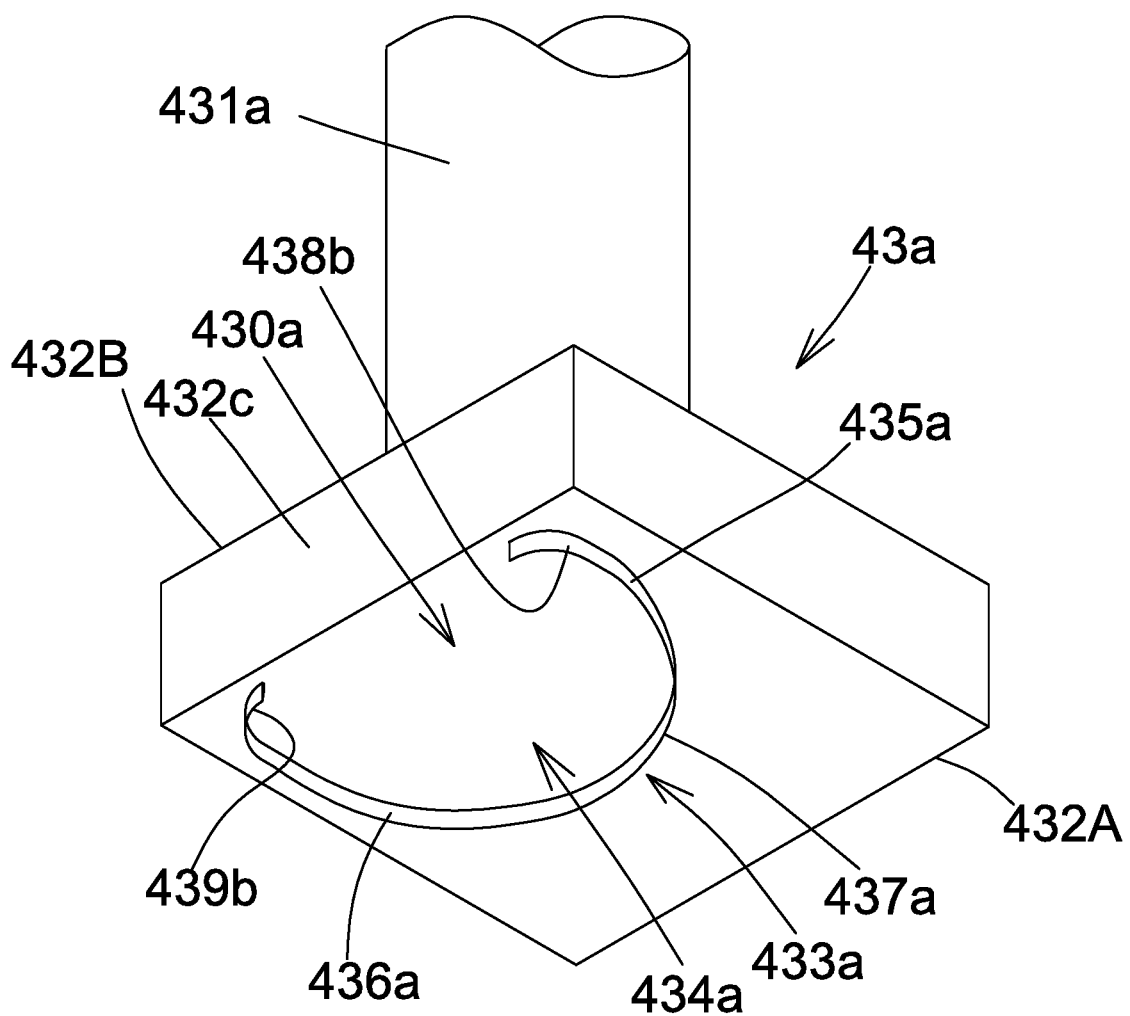
FIG. 12a is a perspective view of a shape cutting unit in accordance with a fourth implementation mode of the present invention.

With reference to FIG. 12a for a shape cutting unit 43a in accordance with the fourth implementation mode of the present invention, the shape cutting unit 43a is modified based on the basic structure of the third implementation mode, and their difference resides on that the cutting knife 433a is in a geometric arc shape, and the geometric arc shape makes the cutting knife 433a to be in a semicircular shape, a semi-elliptical shape, or a half-egg shape. In other words, the central position of the first-end cutter 437a of the cutting knife 433a is formed into the geometric arc shape to constitute an end of the cutting knife 433a, and the side cutters 435a, 436a, the end corner cutters 438b, 439b, and both sides of the first-end cutter 437a are formed into the geometric arc shape to constitute both side edges of the cutting knife 433a, and the gap 430a is formed into the geometric arc shape to constitute the status of the gap at the other end of the cutting knife 433a. Similarly, the gap 430a does not have the installation of the cutting knife 433a.

Figure 12B:
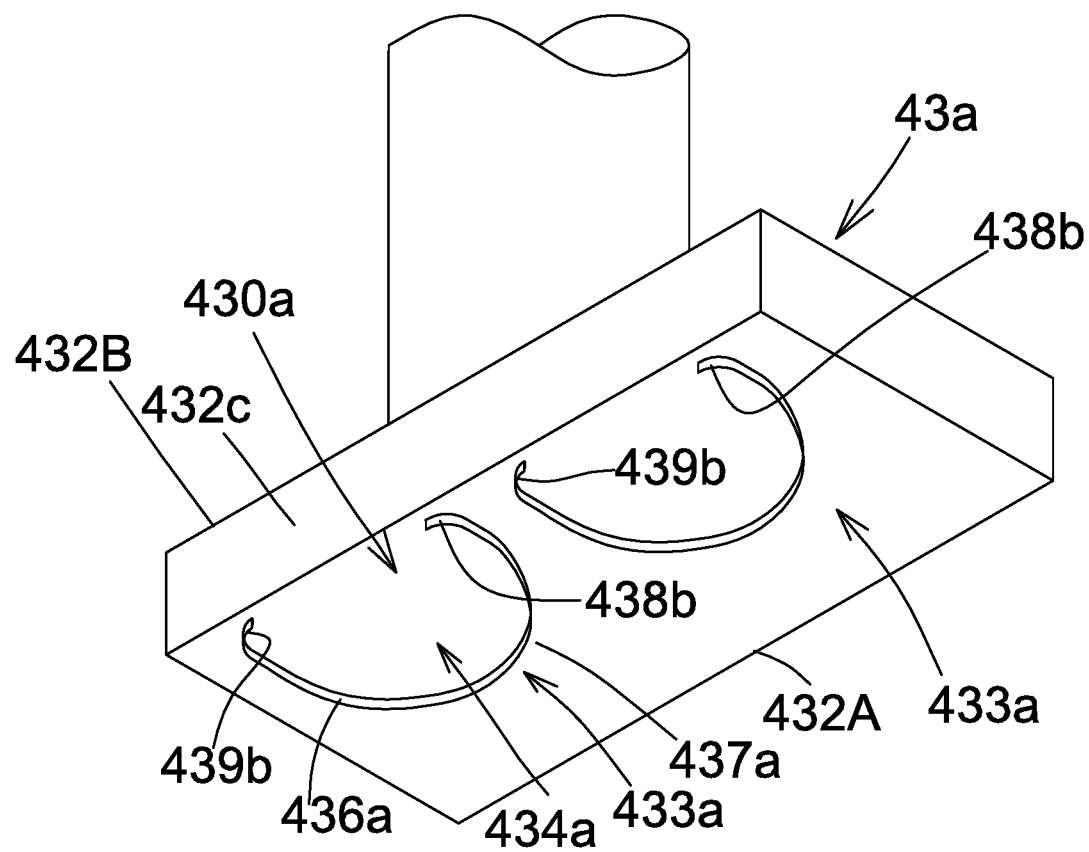
FIG. 12b is a schematic view of a shape cutting unit with a plurality of cutting knives in accordance with the fourth implementation mode of the present invention.

With reference to FIG. 12b for the schematic view of a shape cutting unit 43a installed with a plurality of cutting knives 433a in accordance with the fourth implementation mode of the present invention, two cutting knives 433a are installed on the cutting tool holder 432c, but the quantity of the cutting knives 433a is not limited. The structure of the cutting knife 433a is the same as the structure shown in FIG. 12a, and thus its description will not be repeated.

Figure 13A:
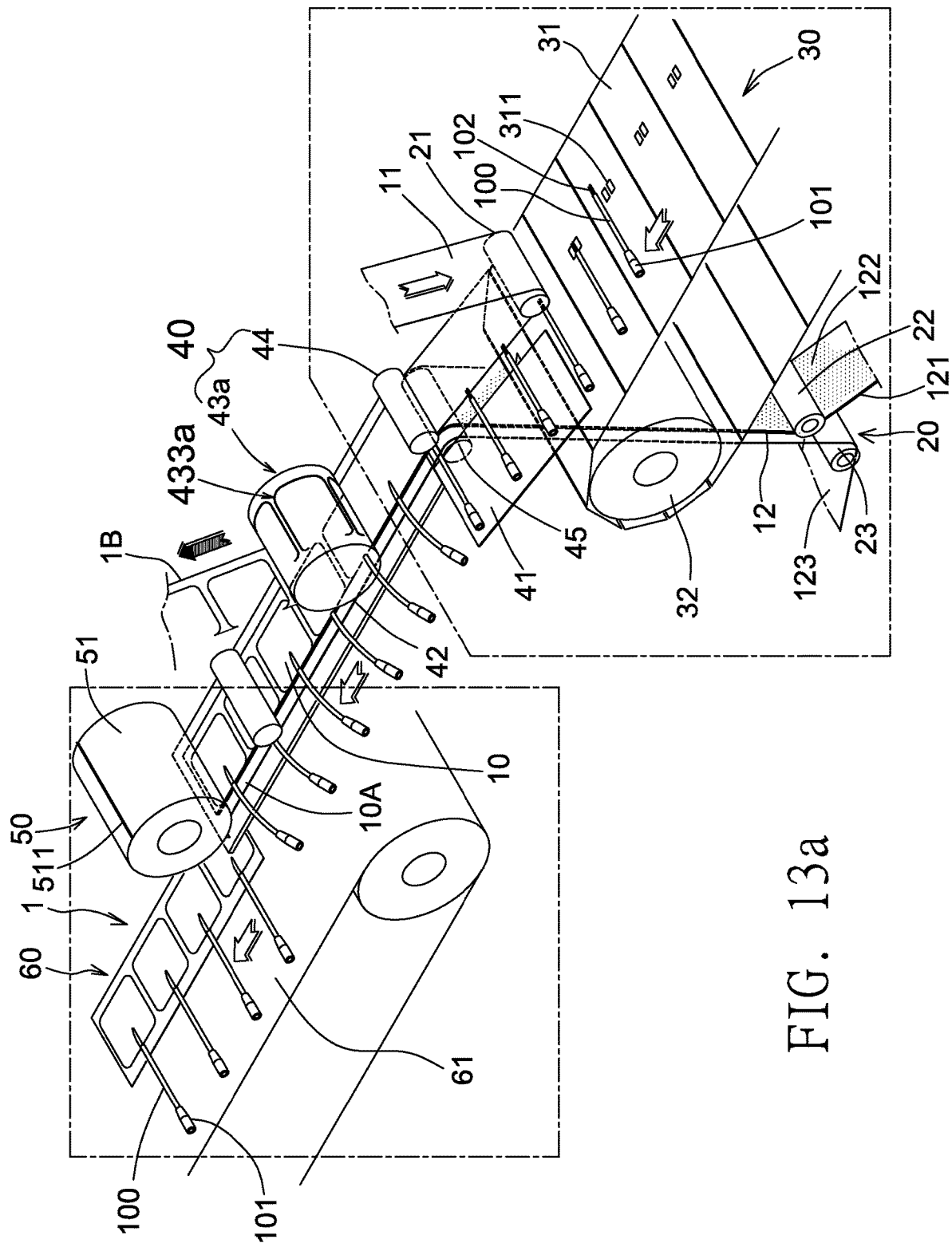
FIG. 13a is a perspective view showing a cutting operation of a shape cutting unit in accordance with a fifth implementation mode of the present invention.
Figure 13B:
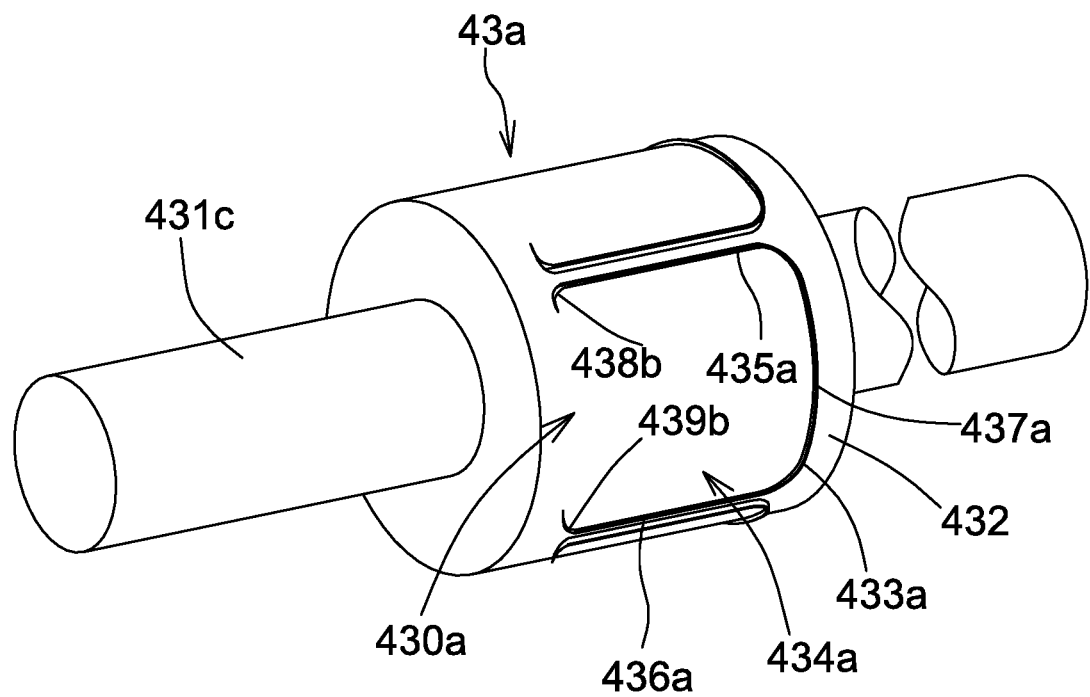
FIG. 13b is a perspective view of a shape cutting unit in accordance with the fifth implementation mode of the present invention.
Figure 13C:
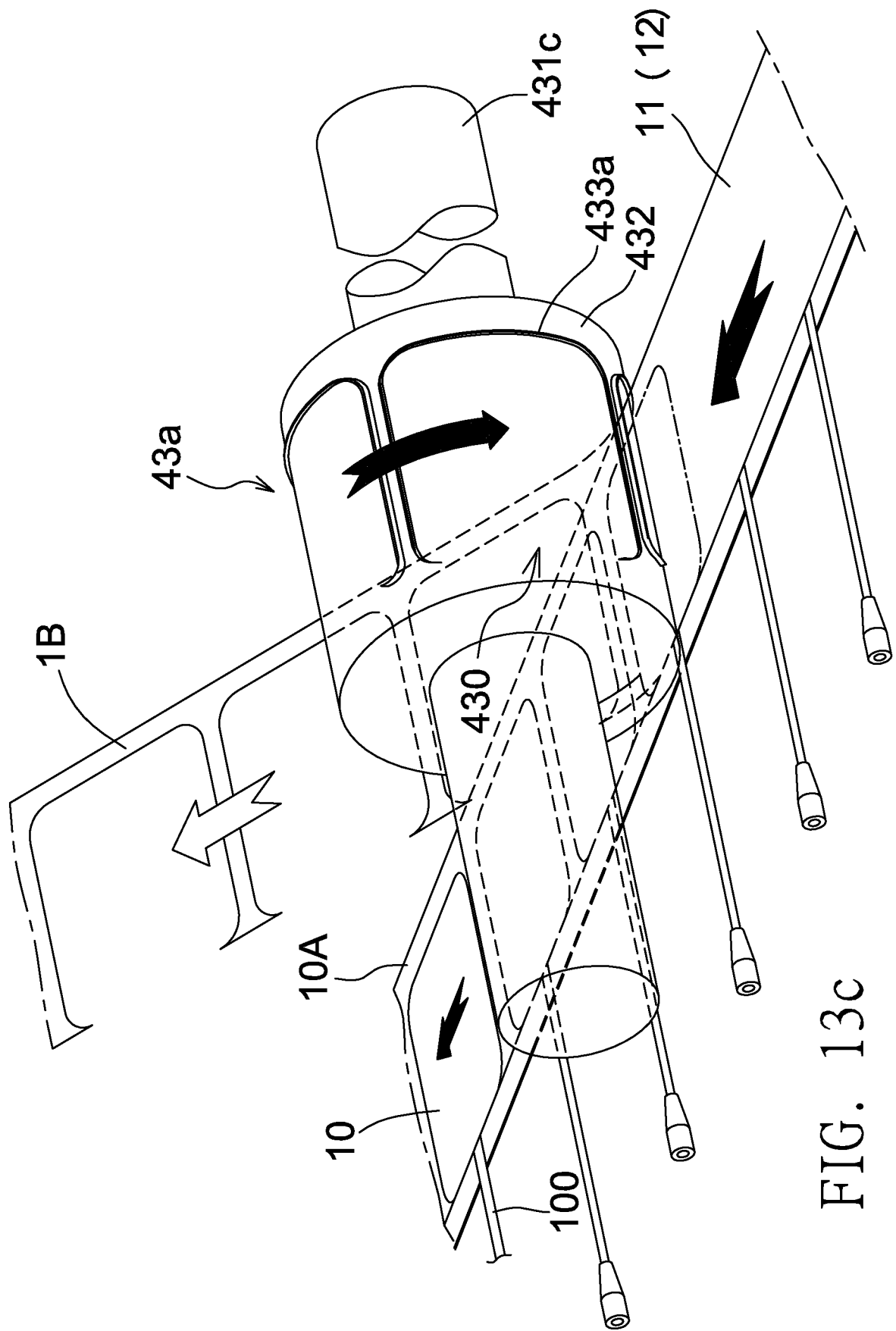
FIG. 13c is a schematic partial view of a cutting operation of a shape cutting unit in accordance with the fifth implementation mode of the present invention.

With reference to FIGS. 13a, 13b, and 13c for a shape cutting unit 43a in accordance with the fifth implementation mode of the present invention, the shape cutting unit 43a is modified based on the basic structure of the embodiment as shown in FIG. 3 and the third implementation mode, and the driving shaft 431 is a transmission shaft 431c for driving a roller body 432, wherein the roller body 432 is installed with at least one cutting knife 433a, and the structure of the cutting knife 433a is the same as the structure of the cutting knife 433a (wherein the numerals representing the respective cutting knives are also the same) of the third implementation mode, and thus its description will not be repeated. In the drawings of this embodiment, a plurality of cutting knives 433a are installed, and the transmission shaft 431c is linked to drive and rotate the roller body 432 in order to perform a cutting operation.

Figure 14:
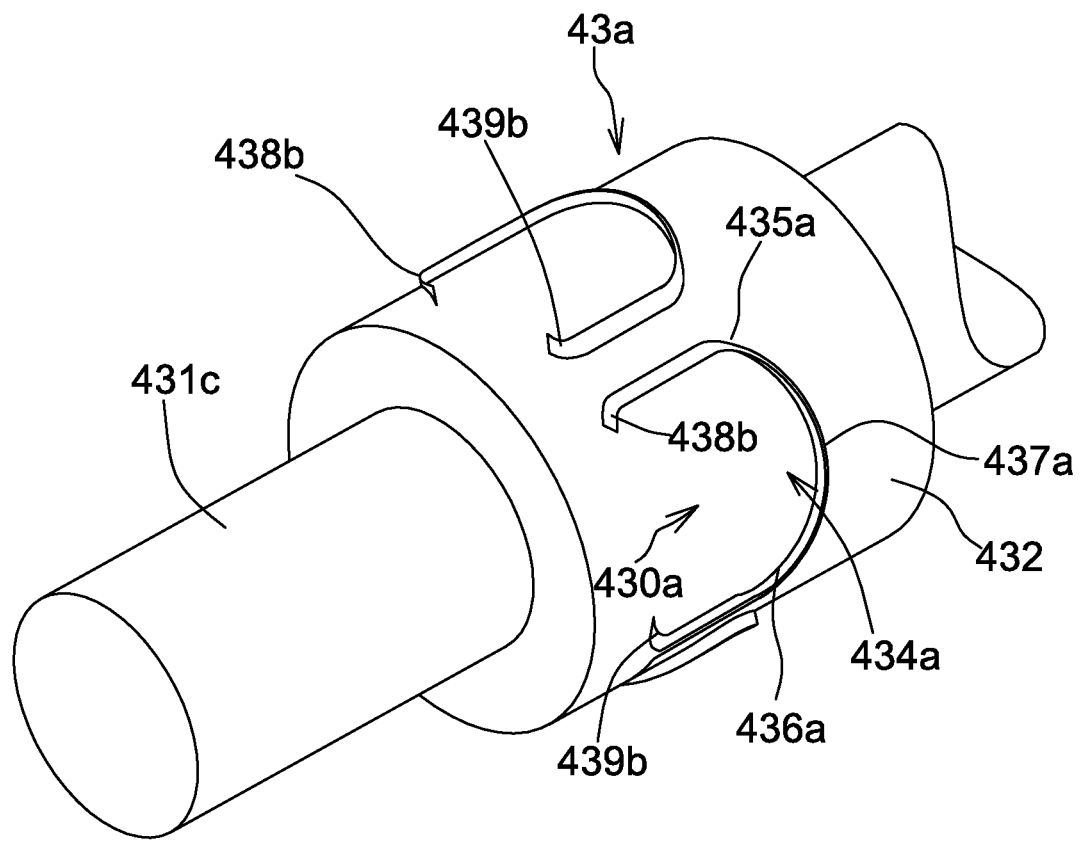
FIG. 14 is a perspective view of a shape cutting unit in accordance with a sixth implementation mode of the present invention.

With reference to FIG. 14 for a shape cutting unit 43a in accordance with the sixth implementation mode of the present invention, the shape cutting unit 43a is modified based on the basic structure of the fifth implementation mode, and their difference resides on that the cutting knife 433a is in a geometric arc shape, and the geometric arc shape makes the cutting knife 433a to be in a semicircular shape, a semi-elliptical shape, or a half-egg shape. In other words, the central position of the first-end cutter 437a of the cutting knife 433a is formed into the geometric arc shape to constitute an end of the cutting knife 433a, and the side cutters 435a, 436a, the end corner cutters 438b, 439b and both sides of the first-end cutter 437a are formed into the geometric arc shape to constitute two side edges of the cutting knife 433a, and the gap 430a is formed into the geometric arc shape to constitute the status of the gap at the other end of the cutting knife 433a. Similarly, the gap 430a does not have the installation of the cutting knife 433a, and the bottom edges of the two end corner cutters 438b, 439b are aligned precisely with or slightly protruded from the strip edge 10B.

With the aforementioned assembly of the shape cutting device of a skin electrode patch of the present invention, the shape cutting device facilitates the electrode lead to be installed conveniently in the production during an electrode patch manufacturing process and has excellent manufacturing efficiency and stable quality. In the meantime, the cutting knife of present invention may be a roller type to provide a design with excellent structural assembly to facilitate the transmission in the whole production line and achieve excellent efficiency for the shape cutting.

What is claimed is:

1. A shape cutting device configured for cutting a skin electrode patch, comprising a stamping shaft and a cutting tool holder coupled to each other, and the cutting tool holder having a cutting tool surface, at least one cutting knife being disposed on the cutting tool surface, and the cutting knife being in a geometric shape, and comprising two protruding side cutters and a first-end cutter, and the first-end cutter being disposed adjacent to an end of the cutting tool holder, and the first-end cutter having at least two opposite ends, and each opposite end of the first-end cutter having a second-end cutter, and the first-end cutter being coupled to the side cutters on both sides, and the two side cutters being coupled to the two second-end cutters respectively, and a cutting area inside the cutting knife being formed and enclosed by the first-end cutter, the two side cutters and the two second-end cutters, and only one gap being formed between the two second-end cutters of the cutting knife and disposed at a non-contact position of the two second-end cutters, and the cutting knife being continuous and complete from a second-end cutter of the two second-end cutters to the other second-end cutter of the two second-end cutters, and the gap being configured for preventing an electrode lead from being cut off.

2. The shape cutting device for skin electrode patch according to claim 1, wherein the cutting tool surface is a horizontal cutting tool surface.

3. The shape cutting device for skin electrode patch according to claim 1, wherein the cutting knife is a square shape or a rectangular shape.

4. The shape cutting device for skin electrode patch according to claim 1, wherein the cutting knife is a circular shape, an elliptical shape, or an egg shape.

5. The shape cutting device for skin electrode patch according to claim 1, wherein the stamping shaft and the cutting tool holder are integrally combined into a stamping shaft body and the stamping shaft body is provided for installing the cutting knife.

6. The shape cutting device for skin electrode patch according to claim 1, wherein the first-end cutter is coupled to the two side cutters through a connection with a fillet or an arc-end angle, and the two side cutters are coupled to the two second-end cutters respectively through a connection with a fillet or an arc-end angle.

7. The shape cutting device for skin electrode patch according to claim 1, wherein the cutting knife is configured to cut an electrode strip, and the electrode strip comprises a coated substrate portion and conductive adhesive portion with equivalent widths and bonded with each other, and a release layer linked with the bottom of the electrode strip, and the release layer is wider than and slightly protruded from the electrode strip.

8. The shape cutting device for skin electrode patch according to claim 7, wherein the coated substrate portion and the conductive adhesive portion have an electrode lead clamped and positioned therebetween, and the electrode lead is protruded out from the electrode strip.

9. The shape cutting device for skin electrode patch according to claim 8, wherein the electrode strip has a strip edge, and the two second-end cutters are aligned precisely with or slightly protruded from the strip edge, and the strip edge is disposed on a side of the electrode strip where the electrode leads are protruding.

* * * * *